United States Patent
Hoegerle

(10) Patent No.: US 8,029,510 B2
(45) Date of Patent: Oct. 4, 2011

(54) SURGICAL MACHINE AND METHOD FOR CONTROLLING AND/OR REGULATING A SURGICAL MACHINE

(75) Inventor: Roland Alois Hoegerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1028 days.

(21) Appl. No.: 11/974,182

(22) Filed: Oct. 10, 2007

(65) Prior Publication Data
US 2008/0077149 A1    Mar. 27, 2008

Related U.S. Application Data

(63) Continuation of application No. PCT/EP2005/004059, filed on Apr. 16, 2005.

(51) Int. Cl.
*A61B 17/00* (2006.01)

(52) U.S. Cl. ............................ 606/80; 335/219; 388/907

(58) Field of Classification Search .................... 606/79, 606/80, 82, 167, 169, 171, 180; 408/8, 9; 318/139; 335/219, 175–179; 324/201; 388/907
See application file for complete search history.

(56) References Cited

U.S. PATENT DOCUMENTS

| 2,244,683 | A |   | 6/1941 | Fisher |
|---|---|---|---|---|
| 3,750,068 | A | * | 7/1973 | Hallin ............................ 335/306 |
| 4,091,880 | A |   | 5/1978 | Troutner et al. |
| 4,204,580 | A | * | 5/1980 | Nalley ............................ 173/48 |
| 4,848,146 | A | * | 7/1989 | Bruno et al. .................... 73/181 |
| 5,107,151 | A |   | 4/1992 | Cambier |
| 5,268,622 | A |   | 12/1993 | Philipp |
| 5,467,911 | A |   | 11/1995 | Tsuruta et al. |
| 5,677,605 | A |   | 10/1997 | Cambier et al. |
| 5,689,159 | A |   | 11/1997 | Culp et al. |
| 5,747,953 | A | * | 5/1998 | Philipp ........................ 318/139 |
| 5,933,339 | A |   | 8/1999 | Duba et al. |
| 5,994,867 | A |   | 11/1999 | Birk et al. |
| 6,013,991 | A |   | 1/2000 | Philipp |
| 6,037,724 | A |   | 3/2000 | Buss et al. |
| 6,059,806 | A |   | 5/2000 | Hoegerle |
| 6,086,544 | A |   | 7/2000 | Hibner et al. |
| 6,101,109 | A |   | 8/2000 | Duba et al. |
| 6,118,932 | A |   | 9/2000 | Maurio et al. |
| 6,249,094 | B1 |  | 6/2001 | Zeh et al. |

(Continued)

FOREIGN PATENT DOCUMENTS

DE    80 00 592    4/1980

(Continued)

OTHER PUBLICATIONS

Ying-Yu Tzou, et al., "FPGA-Based SVPWM Control IC for 3-Phase PWM Inverters" Proceedings of the 22$^{nd}$ International Conference on Industrial Electronics, Control and Instrumentation, Aug. 1996, pp. 138-143 (XP002360956).

(Continued)

*Primary Examiner* — Thomas C. Barrett
*Assistant Examiner* — Christian Sevilla
(74) *Attorney, Agent, or Firm* — Lipsitz & McAllister, LLC

(57) ABSTRACT

In order to so improve a surgical machine comprising a housing and a surgical drive that maintenance of the machine is simplified, it is proposed that the drive and the housing be directly on indirectly connectable in a detachable manner.

A method for controlling and/or regulating a surgical machine is also proposed.

21 Claims, 24 Drawing Sheets

U.S. PATENT DOCUMENTS

| | | |
|---|---|---|
| 6,292,678 B1 * | 9/2001 | Hall et al. ............... 600/374 |
| 6,340,851 B1 | 1/2002 | Rinaldi |
| 6,643,149 B2 | 11/2003 | Arnet et al. |
| 6,819,078 B2 | 11/2004 | Ho |
| 6,885,163 B2 | 4/2005 | Heidrich |
| 7,362,062 B2 | 4/2008 | Schneider et al. |
| 7,422,582 B2 | 9/2008 | Malackowski et al. |
| 7,514,890 B2 | 4/2009 | Schneider et al. |
| 7,740,628 B2 | 6/2010 | Hoegerle et al. |
| 2001/0029315 A1 | 10/2001 | Sakurai et al. |
| 2002/0044472 A1 | 4/2002 | Arnet et al. |
| 2002/0196115 A1 * | 12/2002 | Yamakage et al. ........ 335/302 |
| 2003/0155878 A1 | 8/2003 | Murai |
| 2004/0071003 A1 | 4/2004 | Cocconi |
| 2005/0123408 A1 | 6/2005 | Koehl |
| 2006/0071541 A1 | 4/2006 | Berg |
| 2006/0074405 A1 | 4/2006 | Malackowski et al. |
| 2006/0119305 A1 | 6/2006 | Lee et al. |
| 2007/0147806 A1 | 6/2007 | Schneider et al. |
| 2007/0154192 A1 | 7/2007 | Schneider et al. |
| 2007/0250098 A1 | 10/2007 | Malackowski et al. |
| 2008/0118234 A1 | 5/2008 | Schneider et al. |

FOREIGN PATENT DOCUMENTS

| | | |
|---|---|---|
| DE | 198 46 831 | 4/2000 |
| DE | 202 02 724 | 6/2002 |
| DE | 102 25 857 | 1/2004 |
| DE | 20 2004 006 724 | 7/2004 |
| DE | 20 2004 012 388 | 9/2004 |
| DE | 20 2004 012 389 | 9/2004 |
| DE | 10 2004 020 808 | 11/2005 |
| DE | 10 2004 062 580 | 3/2006 |
| DE | 20 2008 006 868 | 8/2008 |
| DE | 10 2007 039 764 | 12/2008 |
| EP | 1 009 096 | 6/2000 |
| JP | 6-304175 | 11/1994 |
| WO | 96/01521 | 1/1996 |
| WO | 97/50171 | 12/1997 |
| WO | 98/06338 | 2/1998 |
| WO | 03/013372 | 2/2003 |
| WO | 03/052919 | 6/2003 |
| WO | 2004/036755 | 4/2004 |
| WO | 2006/012990 | 2/2006 |

OTHER PUBLICATIONS

Felix Jenny/Dieter Wüest, "Steuerverfahren für selbstgeführte Stromrichter", 1995 vdf Hochschulverlag AG an der ETH Zürich und B.G. Teubner Stuttgart (10 pages).

* cited by examiner

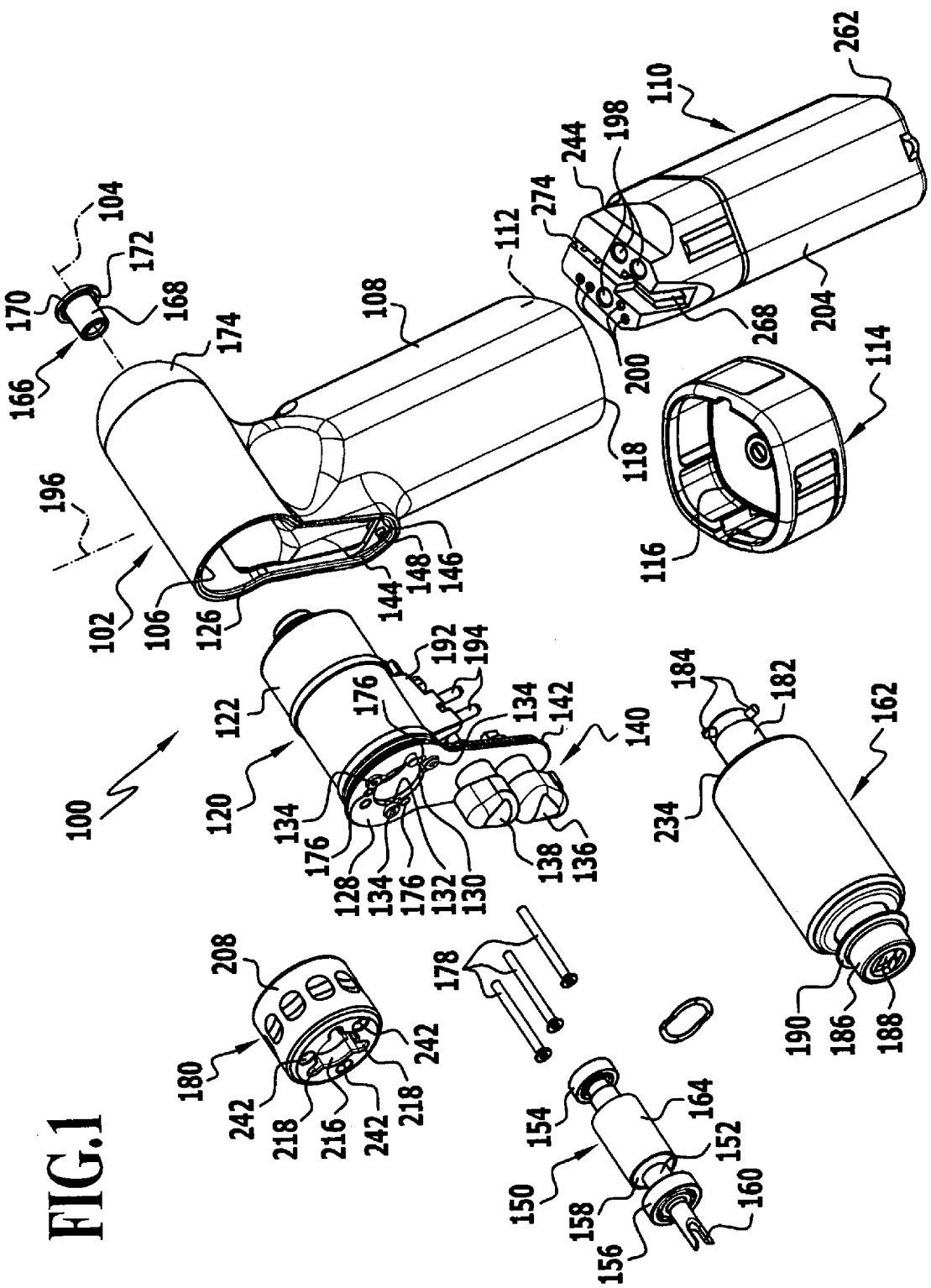

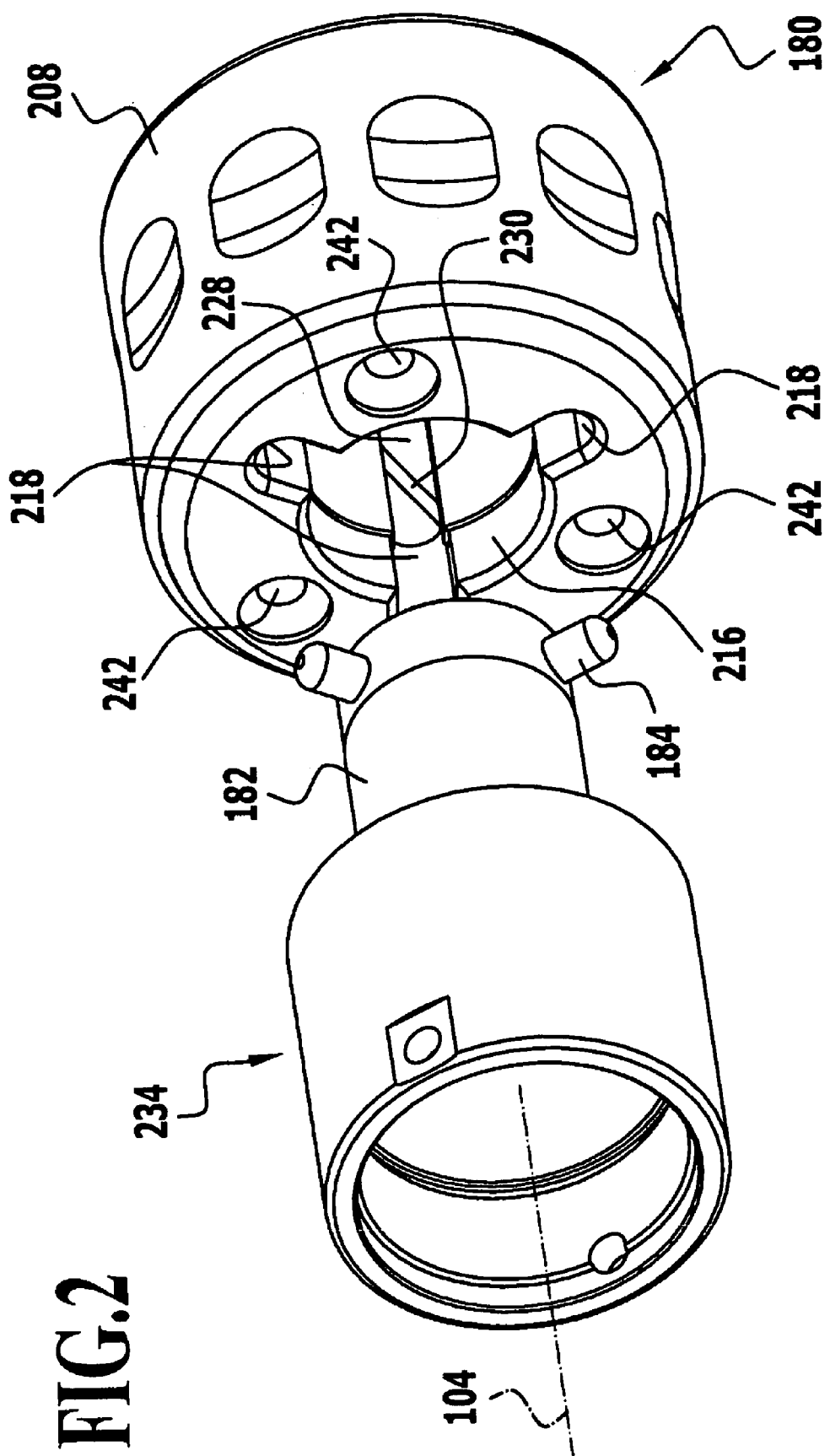

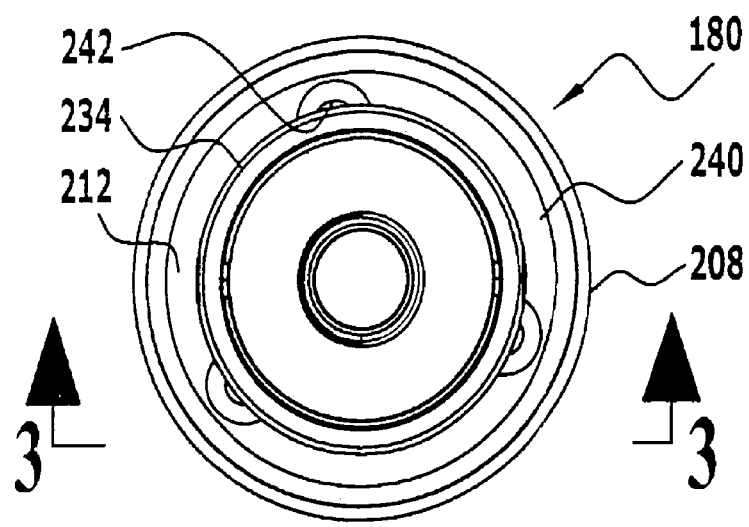
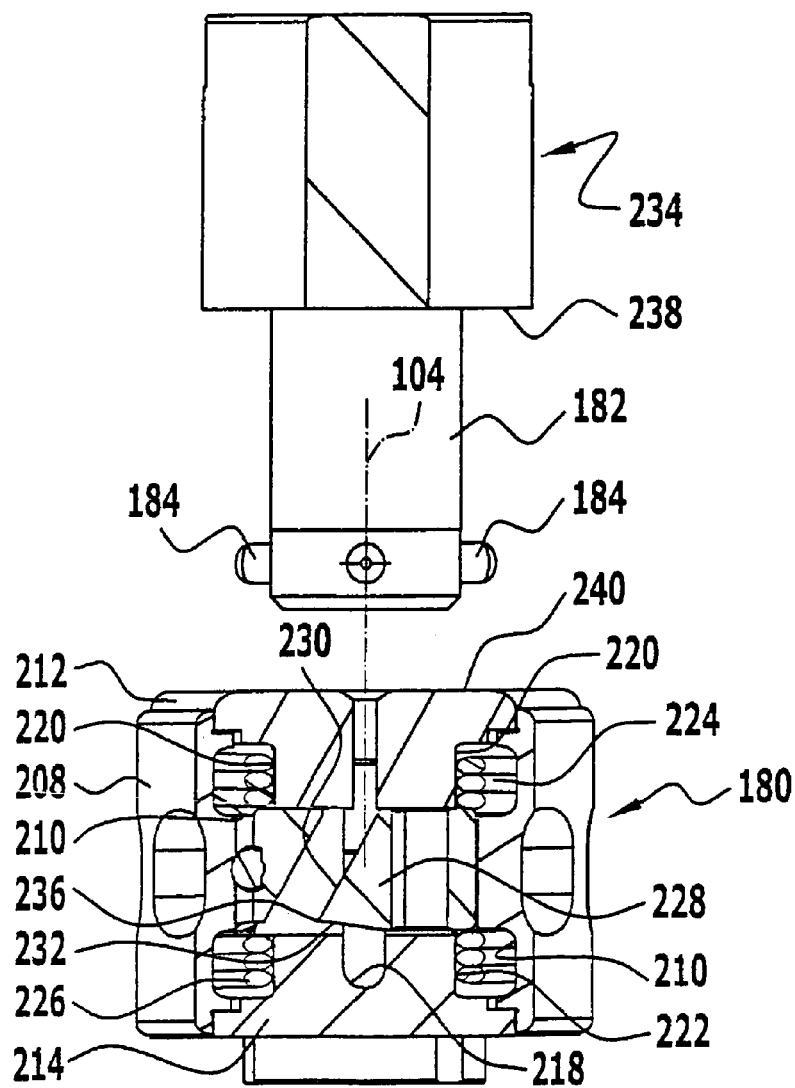

SURGICAL MACHINE AND METHOD FOR CONTROLLING AND/OR REGULATING A SURGICAL MACHINE

This application is a continuation of international application number PCT/EP2005/004059 filed on Apr. 16, 2005.

The present disclosure relates to the subject matter disclosed in international application number PCT/EP2005/004059 of Apr. 16, 2005, which is incorporated herein by reference in its entirety and for all purposes.

BACKGROUND OF THE INVENTION

The present invention relates to a surgical machine with a housing and a surgical drive.

Machines of the kind described at the outset are used in different variants and embodiments in surgery. Examples of such machines are drilling machines, milling machines and saws, in particular, jigsaws and oscillating saws. In some cases, both the design of such machines and their operation are very complicated. Also problems with the maintenance and cleaning of the machines keep recurring.

The object of the present invention is, therefore, to so improve a machine and a method of the kind described at the outset that the machine is easier to handle.

SUMMARY OF THE INVENTION

This object is accomplished in accordance with the invention in a surgical machine of the kind described at the outset in that the drive and the housing are directly or indirectly connectable in a detachable manner.

The surgical machine can thus be disassembled particularly easily, for example, by separating the drive and the housing. The drive can be connected to the housing directly, for example, by corresponding attachment mechanisms or indirectly, for example, by clamping between two elements that are directly connectable to the housing. The drive can thus be detached from the housing in a simple way, for example, for cleaning purposes or for exchange of the motor, in particular, on account of a defect, or for maintenance purposes.

It is advantageous for the housing to comprise at least two openings. For example, the drive can be introduced through one opening of the housing, and a power supply unit of the machine through another opening or the same opening. It is, however, also possible for more than two openings to be provided, for example, three or four, for introducing into or removing from the housing in a simple way further component assemblies or components for assembly or maintenance purposes.

The machine preferably comprises a power supply unit which is introducible into the housing. It is thus possible to operate the machine independently of the mains and therefore dispense completely with cable connections which are required for mains operation.

It is expedient for the machine to be completely washable and/or sterilizable without the power supply unit. It is thereby ensured, on the one hand, that the machine can also be used in sterile areas such as, for example, operating theaters, without the risk of germs being able to enter the sterile area. On the other hand, the machine is thus also prevented from becoming damaged during the cleaning, in particular, in a washing machine or dishwasher.

In principle, it is conceivable to choose a mains-dependent DC voltage source as power supply unit for the surgical machine. It is, however, particularly advantageous for a mains-independent power supply unit to be provided as power supply for the machine. In particular, the use of a battery or a rechargeable accumulator is advantageous. Use of a fuel cell is also conceivable. The machine can thus be used in a desired manner without any annoying cable connections during surgical procedures.

To enable operation of the drive at a desired rotational speed or in a desired direction of rotation, it is advantageous for the machine to comprise a control and/or regulating unit for controlling and/or regulating the drive.

The control and/or regulating unit is preferably a motor controller. This can, for example, be disposed in the housing or directly on the drive.

In accordance with a further preferred embodiment of the invention, it can be provided that the power supply unit and the control and/or regulating unit form a power and control unit which is introducible as a whole into the housing. In this way, it is possible to clean the surgical machine separately from the power supply and the control and/or regulating unit. The provision of a power and control unit also facilitates the assembly and preparation of the machine for a surgical procedure.

A part of the housing preferably forms a receiving space for the drive. Furthermore, it is advantageous for a part of the housing to form a grip of the machine and for the power and control unit to be insertable into the grip. This design permits particularly good handling of the machine, as the power supply unit, which, as a rule, is heavy, can then lie directly in an operator's hand. In addition, the power and control unit can be exchanged in a simple way.

It is advantageous for the power and control unit to comprise charge contacts for connection of the power supply unit to a charger and connection contacts for connection to the drive. In principle, this makes it possible to charge the power and control unit connected to the drive without separating it from the drive. In addition, damage to the motor controller connected to the connection contacts is prevented. In conventional power supply units offered without integrated motor controller, i. e., not as power and control unit, the connection contacts can, in principle, also serve as charge contacts. In the proposed embodiment, additional charge contacts are necessary, but the provision of these makes overall handling of the machine simpler.

For simple and quick charging of the power supply unit, it is expedient for four charge contacts to be provided.

To minimize the number of motor contacts, it is advantageous for the drive to comprise at least two motor windings and at least two motor contacts, each connected to two motor windings.

The drive preferably comprises three motor windings and three motor contacts. In particular, each motor contact can be connected to two motor windings connected via the latter. The motor contacts preferably protrude from the drive in the form of contact pins projecting parallel to one another. As a result, the motor contacts can be connected in a simple way to the connection contacts of the power and control unit, for example, by being simply pushed together.

To increase the stability of the motor contacts, it is expedient for the contact pins to be of solid construction. In addition, the risk of corrosion of the motor contacts is thereby minimized. In comparison with contact pins consisting of a multiplicity of spring elements, a solid contact pin or sleeve-like contact pin which is closed outwardly can be cleaned better as it has no spaces in between or cavities in which germs can settle. Furthermore, both the motor contacts and the charge contacts can be gold-plated, as a result of which resistance of the contacts to corrosion is improved and, consequently, even after frequent cleaning, in particular, sterilizing, of the machines, perfect contact can always be established between the drive and the power and control unit.

To obtain a secure connection between the drive and the power and control unit, it is expedient for the power and control unit to comprise contact sockets corresponding to the contact pins. The power and control unit can thus be connected to the drive by simply pushing them together.

In the case of contact pins of solid construction or contact pins in the form of closed sleeves, it is particularly expedient for the contact sockets to be of substantially hollow-cylindrical construction and to comprise resilient wall portions for holding the contact pins in a clamped manner. By virtue of this configuration, secure contact can be established between the contact sockets and the motor contacts even after frequent exchange of the power and control unit.

In accordance with a preferred embodiment of the invention, it can be provided that the power and control unit comprises a rotational speed prescribing unit with a rotational speed prescribing sensor which is contactlessly actuatable by an actuating member. In this way, electrical connections between the actuating member and the rotational speed prescribing unit are unnecessary. For example, the actuating member can be connected to the housing and thus cleaned together with the machine, whereas the power and control unit can be removed before cleaning the machine. In this way, corrosion and contact problems can be reliably avoided.

In order that the machine can be operated in different operating modes, it is advantageous for the power and control unit to carry at least one operating mode switchover sensor which is contactlessly actuatable by an actuating member. Owing to the contactless actuatability of the operating mode switchover sensor, electrical connections between the actuating member and the motor controller can be dispensed with entirely. Corrosion problems are thus avoided and optimized cleanability of the actuating member is guaranteed.

In principle, it is conceivable for the at least one operating mode switchover sensor to be a Hall sensor, which is contactlessly actuatable by a magnet or a soft iron element. The at least one operating mode switchover sensor is preferably a light barrier, which is contactlessly actuatable by an actuating member. For example, an actuating member mounted on the housing for movement relative to the latter can interrupt or release the light barrier provided on the power and control unit, in order to switch over from a first to a second operating mode, for example.

Expediently, at least one operating mode activating sensor is provided for activating or deactivating a certain operating mode of the machine. For example, a specific operating mode of the machine, for example, oscillatory operation or pilgrim step operation, can thereby be activated or deactivated in a desired manner, in particular, also permanently.

In principle, it is conceivable for the operating mode activating sensor to be a manually actuatable switch element. It is, however, expedient for the operating mode activating sensor to be a light barrier and for the light barrier to be contactlessly actuatable by an operating mode activation actuating member. It is also conceivable to configure the operating mode activating sensor in the form of an inductive or capacitive sensor or switch element.

The light barrier is expediently an infrared light barrier. This allows the operating mode activating sensor and/or the operating mode switchover sensor to be advantageously configured as infrared light barrier. The two sensors can thus also be disposed in a protected manner in a housing which, in particular, is impermeable to optical light. The risk of damage to the sensors during cleaning as well as unintentional touching are thereby avoided.

The drive advantageously carries the operating mode activation actuating member. This enables, when installing a certain drive in the machine, provision to already be made for whether one or more operating modes are activated or deactivated permanently. To this end, the at least one operating mode activation actuating member is, for example, disposed so that it can interact with the operating mode activating sensor. By virtue of the operating mode activation actuating member, a coding of the drive for certain operating modes can be achieved in a simple way.

For a particularly compact design of the machine, it is advantageous for the power and control unit to carry the operating mode activating sensor. An operating mode activating sensor can thus be exchanged in a simple way with the power and control unit, should it be defective. The exchangeability of the power and control unit also has, in addition, the advantage that in the event a part of the power and control unit has a defect, this defect can be eliminated in a particularly simple way by an operator, namely by exchanging the defective power and control unit for a properly functioning power and control unit. Maintenance of the power and control unit can then be carried out separately from the machine, which can be further operated with a further power and control unit.

The housing is particularly robust and resistant to corrosion when it is made of titanium. Furthermore, it is thus also particularly light.

For optimized disassembly of the machine, it is advantageous for a frame which is connectable to the housing to be provided and for the drive to be detachably connectable to the frame. This makes it possible to detach the drive from the housing by detaching the frame from the housing. In particular, when the frame carries further components or component assemblies of the machine, the machine can thus be disassembled in a simple way, for example, for maintenance or cleaning purposes.

In accordance with a preferred embodiment of the invention, it can be provided that at least one actuating member is provided for prescribing a rotational speed and/or a direction of rotation and/or an operating mode of the drive. The actuating member can be, for example, a movably mounted actuating member or an actuating member which is sensitive to pressure, for example, a pressure sensor.

To further simplify the design of the machine, it is expedient for the at least one actuating member to be detachably connectable to the frame for formation of a push-button unit. The at least one actuating member thus becomes part of a push-button unit, which can also be detachable as a whole from the housing. In particular, the at least one actuating member can serve to activate the operating mode switchover sensor and/or the operating mode activating sensor.

In accordance with a further preferred embodiment of the invention, a coupling device can be provided for connection to a surgical tool. By means of the coupling device, the drive of the machine can be connected, in particular, to a surgical tool or also to a gear unit in order to move the tool in a desired manner, for example, in order to make it rotate or oscillate, as is the case, for example, with a saw.

To improve disassembly of the machine, it is advantageous for the coupling device to be detachably connectable to the frame. As a result, it is, for example, possible to remove a rotor of the drive from the latter and from the housing when the coupling device is detached from the frame. In such an embodiment, the coupling device can simultaneously serve as counterbearing for a rotor and can, but does not necessarily have to comprise bearing elements for the latter.

The coupling device expediently comprises at least one locking element for securing a coupling element of the surgical tool or instrument in a coupling receptacle. By means of the locking element, the coupling element of the tool, of a gear unit or of the instrument can be prevented from becoming detached from the machine when it engages the coupling receptacle.

In order to secure the coupling element of the tool, of the gear unit or of the instrument in the coupling receptacle in a simple way, it is expedient for the at least one locking element to be movable transversely to the longitudinal axis of the coupling device, to release, in an insertion position, the coupling receptacle for insertion of the coupling element, and, in a coupling position, to close the coupling receptacle.

In order that a tool or instrument connected to the machine will be unable to become detached in an unintentional manner, it is advantageous for the at least one locking element to assume, in a basic position, the coupling position.

The at least one locking element is preferably held in a resiliently biased manner in the basic position. If the locking element is transferred from the basic position to the insertion position or to any other desired position, then, owing to the resilient bias, the locking element will, after release, be returned to the basic position.

It is particularly advantageous for the at least one locking element to be transferable from the coupling position to the insertion position by introduction of the coupling element into the coupling receptacle. With a coupling device of such configuration, an operator need not actuate any actuating elements, rather, it is sufficient to move the coupling element against the locking element, whereby the latter is automatically transferred to the insertion position, so that the coupling element can be introduced completely into the coupling receptacle for connection of the instrument or tool to the machine.

The locking element can be transferred from the coupling position to the insertion position in a particularly simple way by introduction of the coupling element into the coupling receptacle when the at least one locking element comprises a first slide surface, on which the coupling element can slide for transfer of the locking element from the coupling position to the insertion position. For example, by moving the coupling element parallel to the longitudinal axis of the coupling device, when a slide surface is appropriately provided, the locking element can be moved transversely to the longitudinal direction of the coupling device.

A locking of the coupling element in the coupling receptacle is particularly simple when the locking element has a second slide surface, and when the locking element is mounted so that, after insertion of the locking element into the coupling receptacle, the second slide surface can slide on the coupling element and hold the coupling element free of play in the coupling receptacle. For example, the locking element can be resiliently biased, so that it is moved back into the basic position after introduction of the coupling element into the coupling receptacle, with the second slide surface then sliding on the coupling element and securing the latter in the coupling receptacle, more particularly, free of play, since, owing to the resilient bias, the locking element can be moved exactly far enough for no more play to remain transversely to the direction of movement of the locking element between the coupling element and the coupling receptacle.

A connection of the machine to a tool, a gear unit or an instrument is particularly simple when the at least one coupling receptacle is a recess extending in the direction of the longitudinal axis of the coupling device and bordering on a tool receptacle, arranged coaxially with the longitudinal axis, of the coupling device, and when the at least one coupling element is a projection protruding in radial direction from the instrument or tool and introducible into the coupling receptacle. The instrument or tool to be connected to the machine is introducible with a coupling part parallel to the longitudinal axis into the tool receptacle of the coupling device, and the coupling element simultaneously engages or enters the coupling receptacle.

The design of the tool or instrument and of the coupling device and thus of the machine is particularly simple when the projection is a cylindrical pin. In particular, a locking element can slide particularly well on such a pin.

To ensure a secure connection of the machine to an instrument or accessory part, it is expedient for three coupling receptacles, each with one locking element for one coupling element each, to be provided.

To enable universal use of the machine, it is advantageous for a gear which is detachably connectable to the drive to be provided. For example, an instrument or tool, for example, a drill or a saw blade, can then be connected in a desired manner to the gear. Owing to the detachable connectability of the gear to the drive, the machine can be disassembled in an advantageous way into individual component assemblies.

In order that larger component assemblies can be jointly detached from the housing, it is advantageous for the gear to be detachably connectable to the frame. The gear can then be detached together with the frame from the housing.

Depending on whether a torque provided by the drive or a rotational speed is to be increased or reduced for certain surgical purposes, it can be expedient for the gear to be a step-down or step-up gear.

In accordance with a preferred embodiment of the invention, it can be provided that with the gear a rotational movement of a drive shaft of the drive can be converted into an oscillating movement of a coupling part which is connectable to a tool. This configuration makes it possible to use the machine as, for example, saw. A saw blade can be connected to the coupling part, and owing to the oscillating movement, for example, about an axis of rotation or in a longitudinal direction, both a jigsaw and an oscillating pendulum saw can be provided.

The design of the machine is particularly compact when the coupling part is mounted so that an oscillating movement of the coupling part can take place in an extension of a longitudinal axis of the drive shaft. For example, a jigsaw can be thus configured, and the saw blade can be directly connected in an extension of a longitudinal axis of the drive to the coupling part, which makes a particularly slim design of the machine possible.

The design of the gear for enabling an oscillating movement of the coupling part is particularly simple when the gear comprises an eccentric driven by a cylindrical gear. A rotational movement of a rotor of the drive can thus be converted into an oscillating movement of the eccentric.

In order that an oscillating movement of the coupling part can take place in an extension of a longitudinal axis of the drive shaft, it is expedient for the cylindrical gear to comprise a bevel gear mounted for rotation about an axis transversely to the longitudinal axis of the drive shaft, for the bevel gear to carry the eccentric, and for the eccentric to project parallel to the longitudinal axis of the bevel gear.

In accordance with a preferred embodiment of the invention, it can be provided that at least two closure elements are provided for closing the at least two openings of the housing. On the one hand, parts disposed within the housing are thereby prevented from emerging unintentionally from the latter. On the other hand, the parts, elements or component assemblies of the machine disposed in the housing are protected against external influences.

The design of the machine is particularly simple when the frame forms a closure element.

To prevent germs from penetrating into the interior of the machine or into the interior of the housing, it is expedient for the at least two openings to be sealed in a fluid-tight manner. Inter alia, this makes it possible to clean, in particular, sterilize the machine without the power and control unit. Subsequently, the power and control unit, which does not necessarily have to be or have to be made germ-free, can be inserted into the housing and the opening provided therefor sealed in a fluid-tight manner.

The design of the machine is further simplified when the at least two closure elements close the at least two openings in a fluid-tight manner. Sealing elements, for example, shaped in accordance with a contour of the respective opening can be used for this purpose. These can, for example, be seals of circular cross section or lip seals. O-rings are preferably used when the openings are ring-shaped openings closed within themselves.

The drive of the machine is of particularly robust design when the drive is an electric motor. In addition, the machine can also be employed with an appropriate power supply independently of the mains.

The service life of the machine is increased when the electric motor is a brushless motor. Downtimes owing to repair and maintenance of the machine are thus significantly reduced.

To minimize circuit expenditure and, consequently, be able to construct the motor in a particularly compact manner, it is expedient for the electric motor to be an electronically commutated DC motor.

In principle, it is conceivable to use an electric motor which comprises a Hall system for rotational speed detection. However, additional contacts are then required to connect the motor controller to Hall sensors of the Hall system for rotational speed detection. It is, therefore, particularly expedient for the electric motor to be a sensorless motor. The rotational speed of the motor can then be detected by, for example, determining a CEMF (counterelectromotive force). In particular, a sensorless electric motor is to be understood as no rotational speed detection sensors being provided or disposed on the electric motor for determining an actual rotational speed of the electric motor. Such electric motors are considerably more cost-effective than motors comprising sensors, and, in addition, the overall construction of the surgical machine is simplified. The reason for this is that fewer connections need be provided for the motor. This has the additional advantage that in the case of a surgical machine that can be disassembled no corrosion problems occur with contacts for connecting the motor controller to rotational speed detection and/or position sensors. Such contacts are usually exposed to small voltages or currents, so that even slight corrosion of the contacts can lead to errors in detecting the actual rotational speed of the electric motor. Precisely this cannot happen with a machine according to the invention.

The disassembling of the machine into component assemblies is further improved by a drive unit comprising the drive being provided and by the drive unit being detachably connectable to the frame. For example, further elements can be provided on an electric motor, for example, special motor contacts or attachment elements for attachment to the frame or to the housing, so that the drive unit comprising the drive can then be removed as a whole with the frame from the housing.

To further improve the maintenance friendliness of the machine, it is expedient for the electric motor to comprise a rotor, and for the rotor to be removable from the drive unit parallel to its longitudinal axis after removal of the coupling device and/or the gear disposed on the frame.

In particular, when the rotor comprises a shaft on which bearings, impact elements and a permanent magnet are attached, owing to the design proposed in accordance with the invention the rotor can be easily and quickly exchanged without having to open the housing completely. The magnet provided on the shaft can be a permanent magnet, in particular, a one-part magnet or a magnet comprised of thin individual disks. Here the advantage is that eddy current losses are reduced. If a permanent magnet is used, it preferably has a borehole extending through it and can, consequently, be threaded onto the rotor shaft. This increases the stability and the flexural rigidity of the rotor. To protect the rotor from external influences during cleaning, in particular, during sterilization, a sheath in the form of a thin sleeve made of rustproof, a magnetic material is preferably provided over the magnet mounted on the shaft. The mechanical stability of the rotor, in particular, at high rotational speeds is thereby increased. Furthermore, a protection against corrosion is thus created for the magnet, so that neodymium-iron-boron magnets can also be used.

To hold the drive in a defined and secure manner on the housing, it is expedient for at least one attachment element to be provided. For example, the attachment element can be a screw or a screw sleeve or also a component with which the drive can be connected to the housing by means of a bayonet connection.

To connect the drive particularly easily to the housing, it is advantageous for the attachment element to be provided in an extension of a longitudinal axis of the drive for fixedly connecting the drive to the housing. In particular, the attachment element can also serve to fix an extension sleeve which protrudes from the housing in an extension of the longitudinal axis of the rotor, for example, when a K-wire extending through the entire drive is to be placed with the machine.

The design of the machine is further simplified when the attachment element forms a closure element. The attachment element thus serves to both close an opening and fix the drive to the housing.

The machine can be disassembled particularly simply when the frame is detachable from the housing after removal of the attachment element. For example, the frame can be held in a corresponding recess by tensile forces applied by the attachment element, which pull the frame into the corresponding recess. Detachment of the attachment element then also releases the frame relative to the housing.

In order to be able to perform as wide a variety of surgical procedures as possible with the machine, it is advantageous for the machine to be a drilling or milling machine, a jigsaw or an oscillating saw.

In accordance with a preferred embodiment of the invention, it can be provided that the at least one actuating member mounted movably on the frame or on the housing is sealed in a fluid-tight manner in relation to the frame and/or to the housing. Germs in the area of the actuating member can thereby be prevented from penetrating into the interior of the housing.

A particularly simple and permanently tight connection between the actuating member and the frame and/or the housing is achieved by a bellows seal being provided for the at least one actuating member.

To minimize the number of actuating members and hence also the number of openings or through-holes into the interior of the housing that have to be sealed off, it is expedient for the jigsaw and the oscillating saw to each only have a single movably mounted actuating member for prescribing a rotational speed. A drilling machine, on the other hand, can have, for example, two actuating members, one for prescribing a rotational speed, another for switching over or setting an operating mode of the machine.

To minimize the number of bearings required for a rotor of the drive and to additionally improve its mounting, it is expedient for the jigsaw and the oscillating saw to comprise a drive which has a shaft bearing for a rotor of the drive at one end only, and for a second shaft bearing for the rotor to be provided in a gear unit of the machine. The rotor can then be connected to the gear unit. On the one hand, it can carry a shaft bearing, and, on the other hand, a shaft bearing for the rotor can be provided in the gear. Such a shaft of the rotor could also be referred to as two-part shaft, one part being provided in the drive, another part in the gear.

It is expedient for the drilling or milling machine to have two movably mounted actuating members for prescribing a rotational speed of the drive and for switching the drive over from a first to at least a second operating mode and vice versa.

It is advantageous for a surgical push-button unit for prescribing a rotational speed and/or a direction of rotation of the surgical machine to be provided with at least one actuating member mounted for movement in a direction of actuation. The advantage of such a push-button unit is, in particular, that it can be removed as a whole from the machine, in particular, from the housing, for example, when it is damaged or is to be cleaned separately.

Furthermore, it is expedient for the push-button unit to comprise the frame. If the frame is removable from the housing, this means that the push-button unit is also removable as a whole from the housing. Disassembly of the machine is thereby further simplified.

In accordance with a preferred embodiment of the invention, a field generating unit for generating a magnetic or electric field, and at least one actuating sensor for generating an actuation signal in response to a movement and/or a position of the actuating member can be provided, the generated actuation signal being correlated with a field strength and/or a change in the field generated by the field generating unit, which occurs as a result of a movement of the actuating member. This configuration can, in particular, be contactlessly actuated by the actuating sensor, for example, by a field strength and/or a change in the field generated by the field generating unit being brought about by a corresponding actuating element or actuating member.

There is known, for example, from U.S. Pat. No. 5,747,953 a battery-operated surgical drive unit with a push-button unit in the form of an accumulator machine comprising as field generating unit a magnet which is connected to a push-button of the push-button unit and can be moved relative to a Hall sensor serving as actuating sensor. An actuation signal is generated by changing the spatial distance of the magnet from the sensor. Such an assembly does make it possible, for cleaning purposes, for example, for sterilizing the drive unit, to separate electronics disposed in the drive unit from the push-button unit prior to the sterilization. However, the known construction has the disadvantage that the magnet must also undergo a cleaning cycle. In particular, if it is not completely encapsulated, it can become detached from the push-button. Furthermore, with each connection, the electronics comprising the Hall sensor, and the push-buttons of the push-button unit are faced with the problem of magnet and sensor having to be correctly adjusted relative to each other again. If the drive unit is often disassembled, a misadjustment can occur in the course of time, which can negatively affect the operability of the drive unit. Therefore, in order to guarantee operational reliability of the machine as long as possible, it is advantageous for the actuating sensor to be coupled with the field generating unit, and for a field changing member to be provided for generating a change in the field acting at the location of the actuating sensor and generated by the field generating unit as a result of a movement and/or a changed position of the actuating member. In particular, this configuration makes it possible to remove the actuating sensor together with the field generating unit in a fixed spatial correlation, for cleaning purposes, from the drive unit, so that no tolerance problems can occur with field generating unit and actuating sensor when assembling drive unit and control electronics. In particular, when a number of drive units are used, this has no negative effect when exchanging their control electronics. In addition, the subjecting of the field generating unit to cleaning and sterilization of the drive unit can thus be avoided. Furthermore, the operational reliability is increased as there is no longer any necessity for the field generating unit to be moved relative to the sensor.

Preferably, the actuating sensor and the field generating unit are fixedly disposed relative to each other. All possible disadvantages of disposing actuating sensor and field generating unit for movement relative to each other are thereby completely excluded. Functionability of the push-button unit remains guaranteed, as the field changing member can bring about a change in the field generated by the field generating unit at the location of the actuating sensor, for use with the drive unit.

In principle, the actuating sensor could be an electric or an electromagnetic actuating sensor. However, it is preferably a magnetic field sensor. Any field generating unit that can generate a magnetic field is thus suited for use with the drive unit.

The magnetic field sensor is preferably a Hall sensor. Actuation signals in the form of electric voltages can be generated in a simple way with such a sensor.

It is advantageous for the field changing member to be at least partially magnetically polarizable and to have a magnetic susceptibility $\chi_m$ differing from zero. This makes it possible, when introducing the field changing member into the field generated by the field generating unit, for a flux density to be changed at the location of the actuating sensor, whereby an actuation signal can be generated.

It is particularly expedient for the field changing member to be at least partially diamagnetic, paramagnetic, ferromagnetic, antiferromagnetic or ferrimagnetic. Materials having the aforementioned magnetic properties can bring about a desired change in a magnetic field, in particular, at the location of a magnetic field sensor.

A particularly simple design of the push-button unit is obtained when the field changing member is a soft iron element. It can be manufactured in a simple way and is resistant to conventional cleaning agents used for cleaning the drive unit.

The design of the push-button unit is particularly simple when the field generating unit is a magnet.

In principle, it is conceivable to use an electromagnet as magnet. However, operation of the push-button unit is particularly reliable when the magnet is a permanent magnet. Maintenance intervals are thereby significantly prolonged for the push-button unit.

It is, however, also advantageous for the magnet to be formed by a coil.

To obtain as high a flux density as possible at the location of the actuating sensor, it is advantageous for the actuating sensor to be disposed between poles of the field generating unit.

In particular, in accordance with a preferred embodiment of the invention, it can be advantageous for the actuating sensor to be disposed in a gap of a ring coil.

To additionally obtain an amplification of the actuation signal, it is expedient for a cross section of the field changing member to vary in a direction of actuation of the actuating member. As a result, the volume of the field changing member that is penetrated by a flux of the field is increased following actuation of the at least one actuating member, namely when the field changing member is moved into the field of the field generating unit or moved out of the field.

It is expedient for the cross section to increase. A field changing member with an increasing cross section can be constructed particularly easily.

A particularly good coupling can be achieved between the field generating unit and the actuating sensor when the field generating unit is coupled by a return path system to the actuating sensor. The return path system is advantageously suited for leading a flux of the field generated by the field generating unit directly from the field generating unit to the actuating sensor. Undesired influences of the field generated by the field generating unit on control electronics of the drive unit are thereby avoided.

In particular, in the case of a magnetic field generating unit, it is expedient for the return path system to be a magnetic return path system. For example, a magnetizable material can be used here for producing the return path system, for example, a mechanical coupling.

In accordance with a preferred embodiment of the invention, it can be further provided that the field generating unit, the return path system and the actuating sensor define a recess, and that the field changing member is disposed so that it is at least partially introducible into the recess as a result of movement of the actuating member. A change in the field acting at the location of the actuating sensor can thus be brought about in a simple and reliable manner.

The design of the push-button unit is particularly simple when the recess has a substantially rectangular cross section.

In principle, it is conceivable for the actuating member to drive the field changing member or to be indirectly connected to it. However, the design of the push-button unit is even simpler when the actuating member carries the field changing member.

It is particularly advantageous for the field generating unit to be disposed on the power supply unit. In particular, the field generating unit can be disposed on the power and control unit. As a result, only the field changing member has to be disposed on the actuating member. All other elements, in particular, the field generating unit, can be disposed on the power and control unit. Consequently, no electric contacts are required between the actuating member and the power and control unit in order, for example, to prescribe a rotational speed with the actuating member. Furthermore, manufacturing tolerances can thereby be easily compensated, for example, when the position of the power and control unit, after exchange thereof, is no longer identical owing to exchange for a different power and control unit, i. e., when the field changing member no longer assumes the original position relative to the field generating unit.

It is advantageous for the machine to have at least two different operating modes, a first operating mode position of the at least one actuating member being associated with a first operating mode, and for the at least one actuating member to be rotatable about an axis of rotation from the first operating mode position to a second operating mode position, which is associated with a second operating mode of the machine, to switch the drive unit over from the first operating mode to the second operating mode. Such a configuration of the push-button unit allows a number of functions to be allocated to the actuating member. For example, it can serve as rotational speed prescribing member for prescribing a rotational speed of the drive unit and simultaneously as switch for switching over from a first to a second operating mode.

It can be expedient for two actuating sensors to be provided and disposed so that there is detectable with the one actuating sensor a position of the at least one actuating member in the first operating mode position and/or a movement of the at least one actuating member in the first operating mode position, and with the second actuating sensor a position of the at least one actuating member in the second operating mode position and/or a movement of the at least one actuating member in the second operating mode position. In this way, one can use different actuating sensors for different purposes in dependence upon a required sensitivity. The design of the push-button unit can thus be adapted to special requirements of a circuit that is used or its components.

The electric motor advantageously comprises a rotor and at least two motor windings.

Machines with a power supply which is independent of the mains power supply are being increasingly used in surgery. As a result, converter circuits have to be made available for batteries or accumulators normally used as power supplies, so as to provide time-dependent voltage and current progressions required for operating an electric motor with a plurality of, as a rule, three, motor windings, from the DC voltages supplied by the power supplies.

Owing to the power supply being independent of the mains power supply, the electric motor has to be electronically commutated. However, in particular, at low motor rotational speeds, i.e., at rotational speeds of less than 1000 revolutions per minute, increased demands are made on the motor control and/or regulation. Since, in addition, high demands are made on optimum starting behavior of the motor under load and on its dynamics, and, at the same time, the best possible efficiency at each operating point should be achieved, it is necessary to determine the position or location of the rotor of the motor, which is usually formed by a magnet. Only the precise rotor position makes it possible for the coils referred to as motor or stator windings to be supplied with electric current, in accordance with the purpose, at the required point in time of commutation.

It is known to use sensor systems, for example, digital or analog Hall systems, for position recognition. A disadvantage of these configurations is that position sensors have to be integrated into the motor and connected to the motor controller. Consequently, corresponding contacts have to be provided for each position sensor if the motor controller is not fixedly connected to the electric motor. This may result in contact corrosion during cleaning, in particular, sterilization of the machine, and, in the worst case, in the machine being put out of operation.

It is also known to use sensorless rotor position recognition methods for applications where high requirements are not made on the dynamics, the starting torque and the motor quality in the range of low rotational speeds of the motor. Since in conventional electronic commutation methods for electric motors, one motor winding is always not supplied with electric current, the CEMF (counterelectromotive force) is measured at the motor winding that is not supplied with electric current and is evaluated for determining an actual rotational speed of the motor.

The above-described, known controlling and regulating methods for surgical machines either require increased circuitry expenditure and additional components, in particular, sensor systems with position sensors, or are unsuitable for specifically starting the electric motor from a standstill under load and operating the electric motor at very low rotational speeds with a high degree of running smoothness.

It is, therefore, advantageous to, in particular, so improve a surgical machine that the electric motor is operable with optimum efficiency at low rotational speeds, and a starting of the motor in accordance with the purpose, also under load, is enabled. This is accomplished, in accordance with a preferred embodiment of the invention, for example, in that a space vector pulse width modulation (SVPWM) method for controlling and/or regulating the electric motor, in which all motor windings are able to be simultaneously supplied with electric current, is performable with the motor controller.

The designing of the motor controller so that the surgical machine can be controlled and/or regulated by a space vector pulse width modulation (SVPWM) method improves, in particular, starting of the motor and motor operation at low rotational speeds. The reason for this is, in particular, that differently from a conventional pulse width modulation (PWM) method, all motor windings are simultaneously supplied with electric current. In particular, in an electric motor with three motor windings, this means that not only two, but all three motor windings are supplied with electric current. Therefore, in the case of three motor windings, 60°-phases of a rotor movement of the electric motor relative to the motor windings can be infinitely varied. In conventional pulse width modulation (PWM) methods or pulse width modulation (PWM) methods used so far, a field angle of the stator field could not be infinitely altered, but only in 60°-steps. Accordingly, a considerably smoother running of the motor can be achieved, above all, at low rotational speeds. In addition, the starting of the motor can be quite specifically defined independently of a position of the rotor of the electric motor.

Optimum design of the machine is accomplished when the motor controller comprises a control unit and a power unit. In this way, in particular, power consumption of the machine is minimized when the electric motor is at a standstill.

Electronic commutation can be achieved in a simple way by the power unit respectively comprising two power transistors for each of the at least two motor windings. Thus, positive and negative voltages in relation to a reference potential can be applied in a simple way to the at least two motor windings, even when only one DC voltage source is available as power supply.

The machine is particularly maintenance-friendly when the electric motor is a brushless DC motor. In particular, the electric motor can also be electronically commutated.

In principle, it is conceivable to dispense with determination of the rotor position of the rotor of the electric motor. However, in particular, in order to optimize starting of the electric motor under load, it is expedient for a rotor position of the electric motor to be determinable for controlling and/or regulating the supplying of the at least two motor windings with electric current. With a knowledge of the rotor position, the field angle of the stator field generated by the motor windings supplied with electric current can be infinitely switched further by the space vector pulse width modulation (SVPWM) method so as to obtain optimum efficiency of the motor.

In accordance with a preferred embodiment of the invention, it can be provided that, to determine the rotor position of the electric motor, at least one of the at least two motor windings is separable from a power supply of the machine for a time interval $t_{interrupt}$, that a CEMF (counterelectromotive force) of the at least one of the at least two motor windings is measurable during the time interval $t_{interrupt}$, and that an actual position of the rotor is calculatable from the measured CEMF (counterelectromotive force). In other words, this means that the simultaneous supplying with electric current is briefly interrupted in a specific manner for a certain time interval in the space vector pulse width modulation (SVPWM) method, namely at one, several or all of the motor windings. During the brief interruption, the CEMF (counterelectromotive force) can then be determined at one, several or all of the motor windings, and a position of the rotor relative to the motor windings can be concluded from its size.

A determination of the rotor position can be further improved when all motor windings are simultaneously separable from the power supply of the machine for the time interval $t_{interrupt}$. The CEMF (counterelectromotive force) can thus be simultaneously determined at all motor windings, and any inaccuracies in the determination of the CEMF (counterelectromotive force) at only one motor winding will, therefore, have a less serious effect.

In order that the time interval $t_{interrupt}$ will remain as short as possible, it is expedient for the voltages applied to the at least two motor windings to be measurable before or at the start of the time interval $t_{interrupt}$ or before the measuring of the CEMF (counterelectromotive force), and for that motor winding at which the lowest voltage is measured to be connectable to a prescribed voltage potential. A time for the transient phenomenon of the system is minimized by this procedure, i. e., the CEMF (counterelectromotive force) can be measured after a minimum waiting time.

The design of the surgical machine is particularly simple when the prescribed voltage potential is ground.

In order to further optimize determination of the rotor position, it is advantageous for the motor controller to be so designed that the CEMF (counterelectromotive force) during the time interval $t_{interrupt}$ is not measured until after a transient time $t_{transient}$. In other words, this means that, for example, the supplying of at least one motor winding with electric current is interrupted, i. e., the time interval $t_{interrupt}$ starts, and only after the transient time $t_{transient}$, which is usually shorter than the time interval $t_{interrupt}$, is the CEMF (counterelectromotive force) measured.

To further improve the accuracy with which the rotor position is determined, it is expedient for the motor controller to be so designed that to determine the CEMF (counterelectromotive force), a voltage progression is measurable at the motor winding or motor windings not connected to the prescribed voltage potential, and for the transient time $t_{transient}$ to correspond at least to a time $t_{constant}$ until the voltages applied to the motor winding or motor windings not connected to the prescribed voltage potential are constant or almost constant in the course of time. This configuration allows the transient time $t_{transient}$ to be varied according to requirements. By determining the time $t_{constant}$, the transient time $t_{transient}$ can be set in a specific manner and minimized.

The motor controller is preferably so designed that a constant value is prescribed for the time interval $t_{interrupt}$. The motor controller can thereby be considerably simplified.

In accordance with an alternative embodiment of the machine, it can, however, be advantageous for the motor controller to be so designed that the time interval $t_{interrupt}$ is alterable. In particular, the time interval $t_{interrupt}$ can thereby be increased or reduced if the time $t_{constant}$ is longer than the initially prescribed time interval $t_{interrupt}$.

Optimized operation of the machine can be achieved by the motor controller being so designed that the duration of the time interval $t_{interrupt}$ is so prescribable that during the time interval $t_{interrupt}$, the voltages applied to the motor winding or motor windings not connected to the prescribed voltage potential assume a constant or almost constant voltage value in the course of time. In particular, in the case of short fall times, i. e., when the time $t_{constant}$ is very short, the time interval $t_{interrupt}$ can be adapted accordingly, whereby the interruption in the supplying of electric current to the motor windings becomes minimally short. The running smoothness of the motor, in particular, at low rotational speeds and during the starting, is thereby improved.

The motor controller is preferably so designed that the time interval $t_{interrupt}$ is increasable when the time $t_{constant}$ is greater than the time interval $t_{interrupt}$, and/or that the time interval $t_{interrupt}$ is reducible when the $t_{constant}$ is less than the time interval $t_{interrupt}$. It is thereby ensured that the time interval $t_{interrupt}$ will never be longer than absolutely necessary to determine as accurately as possible the CEMF (counterelectromotive force) for detecting the rotor position.

In principle, it is conceivable to periodically vary the time interval $t_{interrupt}$. It is, however, expedient for the motor controller to be so designed that the time interval $t_{interrupt}$ is alterable stepwise per revolution. In particular, it is expedient for the time interval $t_{interrupt}$ to be stepwise increasable or reducible. In this way, the time interval $t_{interrupt}$ can be altered until it corresponds at least to the time $t_{constant}$, so as to be able to determine the CEMF (counterelectromotive force) safely and accurately.

In accordance with a preferred embodiment of the invention, it may be provided that the motor controller is so designed that a specified position of the rotor is comparable with the actual position of the rotor as determined from the CEMF (counterelectromotive force) measurement, and that a field angle of the space vector pulse width modulation (SVPWM) is adjustable in accordance with the difference determined between specified position and actual position of the rotor. The motor controller thus determines a deviation of the actual position from the specified position of the rotor and adjusts the field angle of the stator field generated by the motor windings on the basis of the position deviation determined. Optimum efficiency of the motor can thus be achieved.

To further increase the accuracy in determining the CEMF (counterelectromotive force), it is advantageous for the motor controller to be so designed that the CEMF (counterelectromotive force) is only measurable after the motor current of at least one of the at least two motor windings has dropped to zero. Any measurement errors caused by the flowing of a motor current when determining a CEMF (counterelectromotive force) can thus be avoided.

It is expedient for the power supply unit and the motor controller to form a unit, and for the unit to be detachably connectable to the machine. This has, in particular, the advantage that all parts of the machine that are sensitive to heat and moisture can be removed for cleaning purposes, for example, for sterilization of the machine. The construction of the motor controller and the mains-independent power supply as a unit shortens the time required for preparing the surgical machine for use.

It is expedient for the motor controller to comprise a connection circuit which does not connect a processor of the motor controller to the power supply unit until the electric motor is connected to the motor controller. As a result, a premature discharge, in particular, self-discharge, of a mains-independent power supply unit, can be avoided. For, processors of motor controllers usually have a considerably higher power consumption than other components of the controller. Self-discharge of the mains-independent power supply unit can be avoided by activation of the motor controller only being made possible after connection of the motor controller to the electric motor.

The design of the surgical machine is particularly simple when the electric motor comprises three motor windings.

Surgical machines of the kind described at the outset are known in a multitude of variants, especially as drilling and milling machines or saws. They are operated by control signals being generated by the motor controller for the electric motor in order to operate it at a certain rotational speed. Depending on the type of electric motor, rotational speeds of up to 70,000 revolutions per minute can be reached. Due to the construction, however, the efficiency of electric motors is not identical, and, in particular, not always optimal, at all rotational speeds.

It is, therefore, advantageous to so improve a surgical machine that, in particular, an efficiency of the electric motor can be optimized essentially over the entire rotational speed range. This can be accomplished, in accordance with a preferred embodiment of the invention, for example, in that an entire rotational speed range of the surgical machine is divided into at least one lower rotational speed range for low rotational speeds and at least one upper rotational speed range for higher rotational speeds than those in the at least one lower rotational speed range, in that the motor controller is so designed that a first controlling and/or regulating method for controlling and/or regulating the electric motor is performable in the at least one lower rotational speed range, and in that a second controlling and/or regulating method for controlling and/or regulating the electric motor is performable in the at least one upper rotational speed range. This has the advantage that controlling and/or regulating methods that are respectively adapted to a rotational speed range of the electric motor can be employed. In particular, it is conceivable for more than two rotational speed ranges to be defined, and for the respectively used controlling and/or regulating method to also be switched over at the respective transition from one rotational speed range to the other. In this way, not only the efficiency of the electric motor can be optimized during operation, but, for example, an actual rotational speed of the electric motor during operation can also be determined in an optimized manner in dependence upon the rotational speed.

It is advantageous for the first and/or the second controlling and/or regulating method to be a pulse width modulation (PWM) method. In particular, DC motors can be operated in a simple and optimized manner with this method. In particular, sinusoidal current and voltage progressions can be generated by superposing a carrier frequency on digital voltage or current signals.

In accordance with a preferred embodiment of the invention it can be provided for the first controlling and/or regulating method to be a space vector pulse width modulation (SVPWM) method in which all motor windings are able to be simultaneously supplied with electric current. The SVPWM method has the advantage over conventional pulse width modulation (PWM) methods that all motor windings are able to be simultaneously supplied with electric current, so that a smooth, jerk-free operation of the electric motor is also possible at particularly low rotational speeds. Furthermore, starting of the motor from a standstill is considerably improved by all motor windings being able to be simultaneously supplied with electric current.

Alternatively, it can be provided in an advantageous manner for the motor to comprise rotational speed detection sensors and for the motor controller to be so designed that the first controlling and/or regulating method is a method for controlling and/or regulating the surgical machine, in which the motor controller provides control signals for the electric motor in dependence upon an actual rotational speed determined with the rotational speed detection sensors. The rotational speed detection sensors may also serve to determine a position of the rotor of the electric motor. Use of rotational speed detection sensors, in particular, at low rotational speeds of the electric motor has the advantage that the rotational speed can be determined considerably more precisely than, for example, by determining a CEMF (counterelectromotive force) generated at the motor winding or windings. In particular, the determination of the CEMF (counterelectromotive force) is more suitable at higher rotational speeds, as higher induction voltages are generated, in this case, and the detected signals can therefore be processed better.

A particularly simple construction of the machine is obtained when a Hall system is provided for detecting an actual rotational speed of the electric motor and when the Hall system comprises the rotational speed detection sensors. Hall sensors as rotational speed detection sensors can be made particularly small and integrated directly into the electric motor.

In accordance with a preferred embodiment of the invention it can be provided that a rotational speed limit value between the at least one lower rotational speed range and the at least one upper rotational speed range is unalterable. In this case, a switchover between the at least two controlling and/or regulating methods can always take place at a desired rotational speed limit value.

In accordance with a further preferred embodiment of the invention it can also be provided that a rotational speed limit value between the at least one lower rotational speed range and the at least one upper rotational speed range is alterable. Depending on the operating situation, it is thus possible to specifically alter a switchover between the at least two controlling and/or regulating methods. Switching points can then be varied in a desired manner.

A constant switchover between the at least two controlling and/or regulating methods can be avoided in a simple way by the motor controller being so designed that a switchover from the first controlling and/or regulating method to the second controlling and/or regulating method takes place at a first switchover rotational speed and a switchover from the second controlling and/or regulating method to the first controlling and/or regulating method takes place at a second switchover rotational speed. Two switching points can thus be defined, namely at the transition from the lower rotational speed range to the higher rotational speed range, and vice versa. It is thus possible to separate the switchover times, i. e., a small variation in the actual rotational speed of the motor does not necessarily immediately result in a switchover to the other controlling and/or regulating method.

In principle, it is conceivable for the first switchover rotational speed to be less than the second switchover rotational speed. It is, however, particularly expedient for the first switchover rotational speed to be equal to or greater than the second switchover rotational speed. A switchover to the higher rotational speed range therefore takes place at a higher switchover rotational speed than the switchover from the higher rotational speed range to the lower rotational speed range. This therefore results in a hysteresis curve, as it were, with a range in which both the one and the other controlling and/or regulating methods are used for certain rotational speeds, but in dependence upon whether the rotational speed of the electric motor increases or decreases.

In principle, it would be possible to so design the machine that an operator prescribes a desired rotational speed range and activates the corresponding controlling and/or regulating method. In accordance with a preferred embodiment of the invention it can, however, be provided that the motor controller is so designed that the switchover from the first controlling and/or regulating method to the second controlling and/or regulating method takes places automatically at the transition from the at least one lower rotational speed range to the at least one upper rotational speed range, and vice versa. With this inventive design of the machine, the operator need only prescribe the rotational speed at which the machine is to operate.

It is expedient for the machine to comprise a first and a second actuating member, and for the motor controller to be so designed that a rotational speed of the drive can be prescribed to the motor controller by actuating the first actuating member. For example, the second actuating member can serve to switch the machine over from a first operating mode to a second operating mode. Preferably, however, the first actuating member could be so designed that it enables a switchover from a first to a second operating mode. This could be achieved by, for example, the actuating member being rotatable about its longitudinal axis. One operating mode could also correspond to a switched-off state of the machine, the second operating mode or the second position of the actuating member to an operating position of the machine in which it is switched on, without it being a question of a special operating mode. It is thus possible to, on the one hand, prescribe a rotational speed of the drive with the first actuating member and, on the other hand, to also switch off the machine permanently in order to minimize risk of injury by a machine that has been put aside and not properly safeguarded.

It can also be advantageous for the motor controller to be so designed that a switchover from a first operating mode to a second operating mode of the drive is possible by actuating the second actuating member. The first operating mode is preferably clockwise operation of the drive, the second operating mode counterclockwise operation of the drive. This configuration allows actuation of the first actuating member for prescribing a rotational speed, with, for example, the drive switching over from clockwise operation to counterclockwise operation upon actuation of the second actuating member.

Furthermore, the motor controller can be so designed that a switchover from one operating mode to another operating mode is brought about by actuating the second actuating member once or by the drive only being operated in the other operating mode so long as the second actuating member is actuated.

In accordance with a further preferred embodiment of the invention, it can be provided that the motor controller is so designed that the drive is operable in clockwise and/or counterclockwise operation and/or in oscillatory operation, during which the drive runs alternately and, in each case, equally long, in different directions of rotation, and/or in pilgrim step operation. In pilgrim step operation, the drive is operated alternately in different directions of rotation, the drive being operated, in each case, somewhat longer in a first direction of rotation than in a second direction of rotation. In pilgrim step operation, a thread can, for example, be cut in a simple way, for which purpose, the drive is always operated somewhat longer in forward direction for cutting the thread than in rearward direction. Oscillatory operation can be advantageous, in particular, when working on surfaces, so as not to allow any onward movement of the instrument or tool connected to the machine.

For switching over operation of the machine from clockwise or counterclockwise operation to oscillatory operation and/or pilgrim step operation, it can be advantageous for the second actuating member to be continuously actuatable at least during a prescribed switchover time. Such a motor controller does not require an actuating member that has to be switched over mechanically from a first position to a second position. In particular, the actuating member can be a pressure-sensitive sensor. If the actuating member is actuated longer than the prescribed switchover time, the machine can then, for example, transfer from clockwise or counterclockwise operation to oscillatory operation or pilgrim step operation.

In order that switchover from running operation, i. e., from clockwise or counterclockwise operation, to oscillatory operation or pilgrim step operation will not be possible, the motor controller can be advantageously so designed that for switching over from clockwise or counterclockwise operation to oscillatory operation or pilgrim step operation the second actuating member is actuatable while the first actuating member is unactuated. A switchover between different operating modes can thus preferably only take place when the first operating member is unactuated, i.e., in particular, when no rotational speed is requested of the drive. This ensures that a switchover can only take place when the drive is at a standstill.

The motor controller is expediently so designed that a duration ranging from 2 to 5 seconds can be prescribed as switchover time. It is preferable for a switchover time of approximately 3 seconds to be prescribed. By prescribing a switchover time in the indicated time range it is ensured that undesired switchover from a first to a second operating mode will not be caused by unintentional actuation of the second actuating member. A switchover must, therefore, be carried out deliberately by an operator.

The motor controller is advantageously so designed that oscillatory operation and/or pilgrim step operation are maintainable even when the second actuating member, after actuation during the prescribed switchover time, is no longer actuated. This allows switchover of the drive permanently to another operating mode. This requires actuation of the second actuating member once only for at least the switchover time.

In accordance with a further preferred embodiment of the invention, it can be provided that the motor controller is so designed that the drive can be switched over from oscillatory operation and/or pilgrim step operation to clockwise or counterclockwise operation by actuating the second actuating member for a duration which is shorter than the prescribed switchover time. As a result, switchover between two operating modes is possible by specific actuation of the second actuating member.

It is expedient for the motor controller to be so designed that the drive can be switched over from oscillatory operation or pilgrim step operation to counterclockwise operation by actuation of the second actuating member for a duration which is shorter than the prescribed switchover time. This makes it possible to switch over specifically from oscillatory operation and/or pilgrim step operation to counterclockwise operation.

In accordance with a preferred embodiment of the invention, it can be provided that the motor controller is so designed that after switchover from clockwise or counterclockwise operation to oscillatory operation or pilgrim step operation, the drive can first be switched over to pilgrim step operation after actuation of the first actuating member. If, for example, the drive is at a standstill, then, after actuation of the first actuating member, for example, to request a certain rotational speed of the drive, first only switchover to pilgrim step operation takes place. It is also conceivable to so design the motor controller that switchover to oscillatory operation first takes place after actuation of the rotational speed request. Switchover between pilgrim step operation and oscillatory operation can take place in dependence upon a duration of actuation of the first actuating member or a requested rotational speed.

The motor controller is preferably so designed that the machine is operable in pilgrim step operation so long as a rotational speed, which lies below a switchover rotational speed, is prescribed with the first actuating member. In this way, by prescribing the desired rotational speed of the drive, switchover between pilgrim step operation and a further operating mode, for example, an oscillatory mode, can be brought about with the first actuating member.

It is expedient for the motor controller to be so designed that the machine can be switched over from pilgrim step operation to oscillatory operation when a rotational speed which lies above the switchover rotational speed is prescribed with the first actuating member. Switchover from pilgrim step operation to oscillatory operation, therefore, takes place simply by increasing the rotational speed request beyond a certain rotational speed.

It is advantageous, in a method for controlling a surgical machine with an electric motor, for the machine to comprise a first and a second actuating member, and for a rotational speed of the electric motor to be prescribed by actuating the first actuating member. Independently of any other method used for controlling the motor, a rotational speed for operating the drive can thus be prescribed with the first actuating member.

Handling of the surgical machine is particularly simple when switchover from clockwise rotation of the electric motor to counterclockwise rotation of the electric motor is brought about by actuating the second actuating member. The switchover can take place when the second actuating member is permanently pressed, or as long as it remains pressed, or by actuating the second actuating member once.

It is advantageous for the machine to be operated in clockwise and/or counterclockwise operation and/or oscillatory operation, during which the electric motor runs alternately and, in each case, equally long in different directions of rotation, and/or pilgrim step operation, during which the electric motor is alternately operated in different directions of rotation, the electric motor being operated, in each case, somewhat longer in clockwise rotation than in counterclockwise rotation. Depending on the purpose to be fulfilled by the machine, it can be operated in the operating mode best suited therefor. For drilling holes, for example, in clockwise operation, for withdrawing a drill, for example, in counterclockwise operation. Oscillatory operation can, for example, be preferably used when machining drill holes or for use of the machine as trephine. Pilgrim step operation as described hereinabove is advantageous when drill holes are to be provided with a thread. A stepwise cutting of the thread is thus possible.

It is expedient, for switching over operation of the machine from clockwise or counterclockwise operation to oscillatory operation or pilgrim step operation, for the second actuating member to be continuously actuated at least during a prescribed switchover time. As a result, switchover cannot occur unintentionally, but only specifically when an operator continuously actuates the second actuating member at least during a prescribed switchover time.

For switchover from clockwise or counterclockwise operation to oscillatory operation and/or pilgrim step operation, the second actuating member is preferably actuated while the first actuating member is unactuated. It is thereby ensured that the drive will be at a standstill when the switchover takes place, i. e., a switchover to another operating mode cannot occur from full operation.

In order to ensure that a switchover between two operating modes will not take place inadvertently; it is expedient for a duration ranging from 2 to 5 seconds to be prescribed as switchover time. It is particularly advantageous for a switchover time of approximately 3 seconds to be prescribed.

It is expedient for oscillatory operation or pilgrim step operation to be maintained even when the second actuating member, after actuation during the prescribed switchover time, is no longer actuated. This enables an operator to concentrate fully on the handling of the machine, in particular, on the prescribing of a desired rotational speed with another actuating member. Switchover from oscillatory operation or pilgrim step operation to clockwise or counterclockwise operation is advantageously brought about by actuating the second actuating member for a duration which is shorter than the prescribed switchover time. In this way, switchover between various operating modes of the machine can be brought about by briefly actuating the second actuating member again.

Furthermore, it is advantageous for switchover from oscillatory operation or pilgrim step operation to counterclockwise operation to be brought about by actuating the second actuating member for a duration which is shorter than the prescribed switchover time. If, for example, an instrument that is connected to the machine seizes during use of the machine, then switchover between the operating modes described hereinabove can be brought about in a simple way.

Expediently, after switchover from clockwise or counterclockwise operation to oscillatory operation or pilgrim step operation after actuation of the first actuating member, switchover to pilgrim step operation takes place first. In this way, with the machine, a hole can be drilled in clockwise operation and the drill withdrawn in counterclockwise operation, for example. Furthermore, after switchover to pilgrim step operation or oscillatory operation mode a thread can be subsequently cut in the drilled hole.

It is advantageous for the machine to be operated in pilgrim step operation so long as a rotational speed which lies below a switchover rotational speed is prescribed with the first actuating member. It is also conceivable to operate the machine in pilgrim step operation when a requested rotational speed lies above a switchover rotational speed.

Furthermore, it can be expedient for the machine to be switched over from pilgrim step operation to oscillatory operation when a rotational speed which lies above the switchover rotational speed is prescribed with the first actuating member. As a result, switchover from pilgrim step operation to oscillatory operation can simply take place by prescribing a desired rotational speed.

The following description of preferred embodiments of the invention serves for more detailed explanation in conjunction with the drawings.

BRIEF DESCRIPTION OF THE DRAWINGS

FIG. 1 an exploded representation of a first embodiment of a surgical machine;

FIG. 2 a perspective view of a coupling device shown in FIG. 1;

FIG. 2a a plan view of the coupling device of FIG. 2;

FIG. 3 a sectional view taken along line 3-3 in FIG. 2a;

FIG. 4b a sectional view taken along line 4-4 in FIG. 4a;

FIG. 5b an exploded representation of the machine shown in FIG. 5a;

FIG. 6 a front view of the machine of FIG. 5a;

DETAILED DESCRIPTION OF THE INVENTION

Figure 4A:
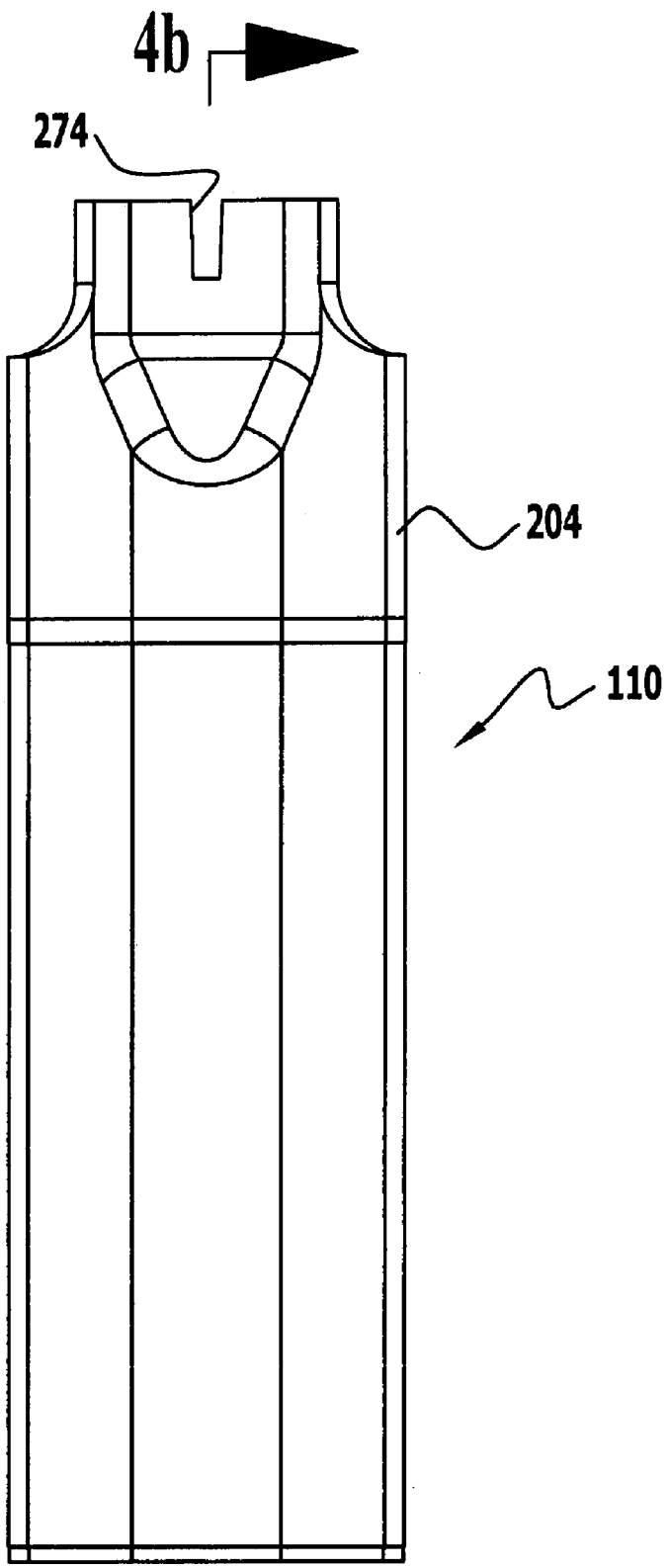
FIG. 4a a side view of a power and control unit.

FIG. 1 shows an accumulator machine in the form of a surgical drilling or milling machine, generally designed by reference numeral 100, which is disassembled into component assemblies described in more detail hereinbelow. The accumulator machine 100 comprises a housing 102 with a motor mount 106 defining a longitudinal axis 104, and an integrally formed grip 108 protruding substantially transversely from the motor mount 106. The grip 108 serves to receive a power and control unit 110, which can be pushed in through an opening 112 of the grip 108, which faces away from the motor mount 106. A cover 114 serves to close the opening 112 and secure the power and control unit 110 in the grip 108. The cover 114 comprises an inside seal 116 which, when the cover 114 is placed on the grip 108, presses against a rim 118 of the grip 108, which surrounds the opening 112. The housing 102 has in the area of the grip 108 a substantially rhombic cross section with rounded-off housing edges. Not shown is a spring that is optionally provided in the grip 108 for aiding removal of the power and control unit 110 after removal of the cover 114.

Coming from the front, a drive unit 120 is insertable parallel to the longitudinal axis 104 into the substantially hollow-cylindrical motor mount 106. The drive unit 120 comprises an electric drive in the form of an electrically commutated sensorless DC motor, which is surrounded by a motor housing 122. A front end opening 126 of keyhole-like shape of the motor mount 106 and of the grip 108 in the area of transition from the motor mount 106 to the grip 108 can be closed with a plate 128 of substantially keyhole-like shape serving as frame. A borehole 130 is provided on the plate 128 concentrically with the longitudinal axis 104. Three cutouts 132 facing towards the front, which border on the borehole 130 and symmetrically surround the borehole 130, are provided for receiving heads of screws 134, with which the drive unit 120 can be fixed to the plate 128 coaxially with the longitudinal axis 104.

Also disposed on the plate 128 are two actuating members in the form of a power/speed push-button 136 and an operating mode selector switch 138, which can both be moved parallel to the longitudinal axis 104 in the direction towards the plate 128 and by means of return springs, not shown, can be transferred to their basic position protruding from the plate 128. The two actuating members form together with the plate 128 a push-button unit 140.

The plate 128 has a circumferential rim 142, which projects transversely to the longitudinal axis 104 and is configured so as to correspond to a rim 144 of the opening 126 that projects in a single step. A seal, not shown, to be inserted between the rims 142 and 144 ensures a germ-free closure of the opening 126 with the plate 128 forming a closure element. Also provided in the proximity of the rim 144 is a short cylindrical pin 148, which protrudes from a stop plate 146 in the direction towards the plate 128 and enters a recess, not shown, of the plate 128 in order to prevent movement of the plate 128 transversely to the longitudinal axis 104.

A rotor 150 of the electric motor can be removed from the drive unit 120 also when the latter is fixed to the plate 128, namely through the borehole 130. The rotor 150 comprises an elongated, substantially cylindrical bearing shaft 152, to which an end ball bearing 154 and a front ball bearing 156 are attached for rotatable mounting of the rotor 150 in the motor housing 122. There is, furthermore, fixed between the ball bearings 154 and 156 on the bearing shaft 152 a permanent magnet 158, which, for this purpose, is provided with a longitudinal bore extending parallel to the longitudinal axis 104. Any necessary balancing elements for balancing the rotor 150 can also be attached to the bearing shaft 152. At its end protruding from the front ball bearing 156, the bearing shaft 152 is constructed in the form of a fork-shaped coupling piece 160, which can engage in a positively locked manner an identically constructed coupling piece, not shown, of a further shaft connected to the latter and can cause this further shaft to rotate.

The permanent magnet 158 can be of one-piece construction or made up of individual disks. In this way, eddy current losses can be reduced. Both the stability and the flexural rigidity of the rotor 150 are increased by the threading of the bored permanent magnet 158 onto the bearing shaft 152. A rotor armoring 164 is provided to protect the permanent magnet 158, namely in the form of a thin sleeve made of rust-proof and non-magnetic material surrounding the permanent magnet 158. The rotor armoring 164 serves to increase the mechanical strength of the rotor 150, which is important, in particular, at very high rotational speeds. Furthermore, the rotor armoring 164 forms a protection for the permanent magnet 158 against corrosion, so that, in particular, also neodymium-iron-boron magnets which are susceptible to corrosion can be used.

The ball bearings 154 and 156 have radial grooves, not shown, on the outer ring, on which damping elements can be mounted. The resulting mounting is thereby made easier to disassemble and reassemble for maintenance purposes than a damping element mounted in the motor housing 122, which is difficult to access. Emergency running properties of the motor are improved by using ceramic ball bearings or ball bearings with individual ceramic components.

A borehole provided at a semicircular end of the motor mount 106 opposite the opening 126 and extending coaxially with the longitudinal axis, through which an attachment screw 166 is introducible with its externally threaded section 168, serves to fix the drive unit 120 in the motor mount 106. A head 170 of the attachment screw 166 can be sealed off in a fluid-tight manner in relation to the housing 102 by a sealing ring 172.

The externally threaded section 168 can be screwed to an internally threaded section, not shown, at the rear end of the motor housing 122. When the drive unit 120 fixed to the plate 128 is pushed into the motor mount 106, it is then drawn, by screwing to the attachment screw 166, against the rear end 174 of the motor mount 106 and hence the rim 142 against the rim 144. Thus, solely by releasing the attachment screw 166 the plate 128 with the drive unit 120 can be detached from the housing 102 and taken out of it.

Provided adjacent to the cutouts 132 on the plate 128 are three threaded bores 176 whose internal threads correspond to externally threaded sections of long-shafted screws 178, with which a coupling device 180 can be fixed to the plate 128. The coupling device 180 serves to connect a coupling piece 182 with three coupling elements 184 protruding from the latter in the form of short cylindrical pins. The coupling piece 182 forms a rear end of a gear block 162, at the front end of which a coupling piece 186 is provided with a tool receptacle 188 for receiving an instrument or tool for connection to the gear block 162. By means of a quick-acting mechanism, not described in more detail, a tool can be released from the tool receptacle 188 by pulling back an outer actuating sleeve 190 with a ring flange in the direction towards the coupling device 180.

Protruding from the motor housing 122 in the direction towards the grip 108 is a contact block 192, from which, in turn, three motor contacts 194, aligned in parallel with one another, protrude, which are each connected to two of a total of three motor windings 199. The motor contacts 194 are in the form of hollow contact pins, which have transverse boreholes, through which the motor windings are threaded and soldered. The contact block 192 serves as mount for the motor contacts 194 and is made of a high-temperature-resistant plastic material. Furthermore, it is sealed off in relation to the motor housing 122. The motor contacts 194 are aligned parallel to a longitudinal axis 196 of the grip 108.

The power and control unit 110 shaped in accordance with the grip 108, which is non-circular inside, has three connection contacts 198, which correspond to the motor contacts 194, and into which the protruding motor contacts 194 extend when the power and control unit 110 is pushed into the grip 108. A secure contact is achieved by the connection contacts 198 being built with limited movement, i. e., floatingly, into the power and control unit 110. Dimension, shape and position tolerances of the connection contacts 198 relative to the motor contacts 194 can, therefore, be compensated. Transition resistances between the connection contacts 198 and the motor contacts 194 are thereby prescribed in a defined manner. Furthermore, the power and control unit 110 can be easily pushed into the grip 108 and also removed from it again. There are also provided on the power and control unit 110 four charge contacts 200, by means of which the power and control unit 110 can be connected by connection cables or by a direct connection to a charger 202 for charging accumulator cells 206 disposed in a sleeve-like housing 204 of the power and control unit 110.

It will now be explained in more detail with reference to FIGS. 2, 2a and 3 how the coupling device 180 functions.

The coupling device 180 comprises a rotary ring 208 having two symmetrically disposed ring grooves 210 open in the direction towards the longitudinal axis 104. Inserted into the rotary ring 208 from both sides are rotationally symmetrical coupling members 212 and 214, which define a hollow-cylindrical coupling receptacle 216 extending through the coupling device 180 coaxially with the longitudinal axis 104, and which are rotationally fixedly connected to each other. The coupling receptacle 216 serves to receive the coupling piece 182. Three coupling receptacles 218 extending from the coupling receptacle 216 parallel to the longitudinal axis 104 serve to receive the coupling elements 184, so that these, coming from the front, enter the coupling receptacle 218 from the side. There are furthermore provided on the coupling members 212 and 214 cutouts 220 and 222, which are located opposite the ring grooves 210 and together with these define two ring spaces, in each of which a helical spring 224 and 226 is mounted. One respective end of the helical springs 224 and 226 is rotationally fixedly connected to the rotary ring 208, the other respective end of the helical springs 224 and 226 to the coupling members 212 and 214. The coupling receptacles 218 do not extend through the entire coupling device 180, but end blind in the coupling member 214.

Rotationally fixedly connected to the rotary ring 208 are three locking elements 228, which, upon rotation of the rotary ring 208 relative to the coupling members 212, are moved in circumferential direction. They have two edges, each extending transversely through a coupling receptacle 218, namely a first slide edge 230 and a second slide edge 232. The first slide edge 230 is turned through an angle of approximately 30° relative to the longitudinal axis 104, the second slide edge 232, which faces in the direction towards the plate 128, through an angle of approximately 90°.

If the coupling piece 182, which is disposed on an end sleeve 234 of the gear block 162, is introduced into the coupling receptacle 216 so that the coupling elements 184 enter the coupling receptacle 218, the coupling elements 184 then first abut on the first slide edge 230. If the coupling piece 182 is moved further into the coupling receptacle 216, the first slide edge 230 then slides on the coupling elements 184, whereby these are displaced against the spring forces of the helical springs 224 and 226 in circumferential direction together with the rotary ring 208 against the coupling members 212 and 214. Once the coupling elements 184 are pushed over an edge 236 connecting the two slide edges 230 and 232 to each other, the helical springs 224 and 226 force the locking elements 228 back again in circumferential direction into their basic position. The second slide edge 232 is moved by the spring forces along the coupling elements 184 and forces these even further into the coupling receptacle 218. A ring edge 238 of the end sleeve 234 facing towards the coupling device 180 abuts on an end face 240 of the coupling device 180, and the second slide edge 232 holds the coupling elements 184 under tension parallel to the longitudinal axis 104 so that the ring edge 238 is held free of play on the end face 240.

To release the gear block 162, the rotary ring 208 need only be turned against the spring forces of the helical springs 224 and 226 relative to the coupling members 212 and 214 until the locking elements 228 release the coupling receptacles 218 so that the coupling elements 184 can be pulled out of these again parallel to the longitudinal axis 104.

The coupling members 212 and 214 are provided with three through-bores 242 extending parallel to the longitudinal axis 104, through which the screws 178 can be inserted and screwed to the threaded bores 176 of the plate 128. In this way, the coupling device 180 can also be released from the plate 128 when the latter is connected to the housing 102. When the coupling device 180 is released from the plate 128, the rotor 150 can then be pulled out of the drive unit 120. Therefore, for maintenance of the ball bearings 154 and 156, the plate 128 need not be released, removal of the coupling device 180 is sufficient.

The design of the power and control unit 110 will now be explained in more detail with reference to FIGS. 4a and 4b.

Figure 4B:
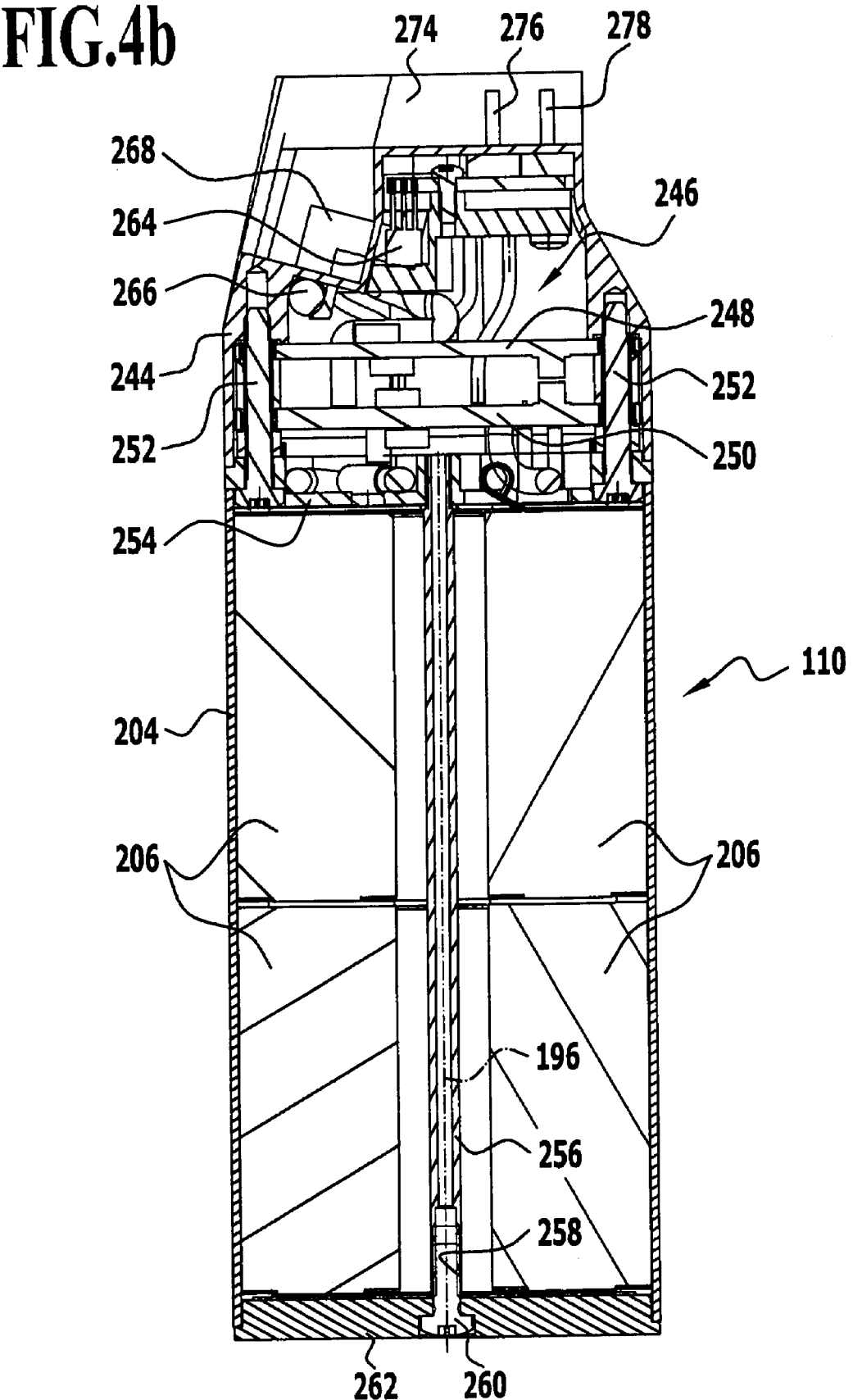

In an end area, facing in the direction towards the motor mount 106, of the housing 204, the so-called control housing 244, a motor controller 246 is disposed, which, in particular, comprises the printed circuit boards 248 and 250 shown in FIG. 4b, on which the electronic components required for controlling the accumulator machine 100 are disposed. The control housing 244 is fixedly connected to the housing 204. Screws 252 serve to secure the motor controller 246 in the control housing 244. A separating plate 254 separating the motor controller 246 from the accumulator cells 206 can be screwed with screws 252 to the control housing 244. A hollow bar 256 projects from the separating plate 254 parallel to the longitudinal axis 196 and extends through the housing 204 as far as the end of the latter. At its end facing way from the motor controller 246, the bar 256 is provided with an internally threaded section 258. By means of a screw 260, a matching housing cover 262 for closing the housing 204 can be connected to the housing 204, which at its other end is connected to the control housing 244. Except for the connection contacts 198 and charge contacts 200 that are led out, the power and control unit 110 is completely encapsulated.

In particular, there are disposed within the control housing 244 a Hall sensor 264 and a bar magnet 266 coupled with the Hall sensor 264 by a return path system described in more detail hereinbelow with reference to FIGS. 21 and 22. The return path system is disposed on either side of a gap 268 in the control housing 244, so that a magnetic soft iron element 270 of parallelepipedal shape disposed on the power/speed push-button 136 can enter an opening 272 formed by the return path system and change a magnetic flux in the return path system. In this way, for example, a rotational speed prescribing signal can be transmitted to the power and control unit 110 without any direct electrical connection between the power/speed push-button 136 and the power and control unit 110.

Furthermore, a narrow slot 274 disposed parallel to the gap 268 is provided on an upper side of the control housing 244. Provided on either side of the slot are two light barriers 276 and 278 extending through the latter, which are either operated by visible light, in which case corresponding cutouts are then provided in the control housing 244, or are formed by infrared light barriers, in which case no openings are then required in the control housing 244. The light barrier 276 serves as operating mode switchover sensor, which can be contactlessly actuated from an end of the operating mode selector switch 138 projecting into the housing 102, namely when the end is moved so far into the slot 274 that the light barrier 276 is interrupted.

The light barrier 278 serves as operating mode activation sensor, which is contactlessly actuatable by an operating mode activation actuating member, not shown. This can, for example, be disposed on the drive unit 120, or not, and, when present, enters the slot 274 and interrupts the light barrier 278. For example, a certain operating mode can thereby be specifically activated or deactivated, in particular, an oscillatory operation of the accumulator machine 100.

The power and control unit 110 described hereinabove can be used for different machines, in particular, also for the embodiments described hereinbelow and not only for the accumulator machine 100. In particular, the power and control unit 110 can be of shorter construction than shown in FIG. 4b, in particular, when only two accumulator cells 206 are disposed below the separating plate 254. The housing 204 can then be shortened accordingly. Similarly, the grip 108 of the housing 102 can then also be shortened accordingly. In particular, when users desire lighter machines or lower capacities are required for operating the accumulator machine 100, a shortening of the grip 108 in the described manner is appropriate.

Due to provision of the housing 204 in conjunction with the detachable housing cover 262, the accumulator cells 206 are directly accessible and hence easy to exchange, which is necessary at regular intervals owing to the normally limited life span of the accumulator cells 206.

As indicated hereinabove, all electronic components of the accumulator machine 100, in particular, the motor controller 246, are accommodated in the power and control unit 110, which does not undergo sterilization. The sensitive electronics are, therefore, not exposed to any harmful environmental conditions, in particular, heat and moisture in a sterilizer. Furthermore, it is not necessary to overly protect these from soiling or to additionally encapsulate them. The electronics of the accumulator machine 100 can also contain in addition to the motor controller 246 the described sensors for controlling rotational speed, direction of rotation and operating mode. Furthermore, monitoring elements for the accumulator cells 206 and communication elements to the charger 202 can be provided. Since the entire sensor technology of the accumulator machine 100 is of contactless design, no movable mechanical elements are provided on the power and control unit 110. In particular, the power and control unit 110 carries no mechanical elements for resetting the actuating members, i. e., in particular, the power/speed push-button 136 and the operating mode selector switch 138, whereby the actuating forces for the actuating members are minimized. The motor controller 246 comprises programmable Hall ICs, so that a slight pushing, for example, of the power/speed push-button 136, first results in an increase in the rotational speed proportionally to the push-button path of the power/speed push-button 136 and only subsequently in an overproportional increase in the rotational speed of the motor up to the maximum rotational speed.

To minimize the power consumption of the accumulator cells 206, in particular, when a machine is not in use, i. e., to keep the quiescent current consumption as low as possible and hence counteract a creeping discharge, the power and control unit 110 is only placed in an operable state under certain conditions. This can, for example, be the case when the power and control unit 110 is pushed into the grip 108, and the connection contacts 198 are in contact with the motor contacts 194. To check this condition, the motor controller 146 is activated periodically, for example, at an interval of one second to ten seconds, preferably six seconds, for a few milliseconds, and inquires the prescribed conditions for activation. If these do not apply, the motor controller 246 is deactivated again.

Cell blocks of widely differing technology are used as accumulator cells 206. By selection of accumulator cells 206 of suitable size and series connection of individual accumulator cells 206, accumulator packs are created, which have both the necessary dimensions and a prescribed nominal voltage of preferably 14.4 volts. Depending on the application profile, this makes it possible to employ cells with lithium ions, lithium polymer, NiMH and NiCd technology. For example, twelve NiMH cells with 1.2 volts each and hence a total voltage of 14.4 volts can be used in cases where it is a question of a high capacity. In contrast, four lithium-ion cells with a nominal voltage of 3.6 volts each, i. e., together likewise 14.4 volts, can be used alternatively for applications where it is a question of a particularly low weight of the accumulator machine 100. Furthermore, lithium-ion cells on the basis of manganese can also be used, as a result of which an external protective wiring of the power and control unit 110 can be dispensed with.

A second embodiment of a surgical machine in the form of a jigsaw 300 is shown in FIGS. 5a to 8a. A large number of the components and component assemblies of the jigsaw 300 correspond to components or component assemblies of the accumulator machine 100, as is clearly apparent from a comparison of the Figures. In particular, the housings 102 and 302 are identical, and also the power and control unit 110, not shown in FIGS. 5a to 8a, which is designed in like manner to that in the accumulator machine 100 and can be held in the grip 308 of the housing 302 with a cover, not shown, which is identical to the cover 114.

The housing 302 comprises a motor mount 306 defining a longitudinal axis 304, and a grip 308 protruding substantially transversely from the motor mount 306 and defining a longitudinal axis 396. A drive unit 320 can be pushed parallel to the longitudinal axis 304 into an opening 326 defined on the front side of the housing 302 in the area of the motor mount 306 and the area of transition to the grip 308. The drive unit 320 comprises a motor housing 322, which is detachably fixable to a plate 328 corresponding in design to the opening 326. The motor housing 322 extends somewhat with a sleeve-shaped section 324 through a circular opening of the plate 328. A power/speed push-button 336 is movably mounted on the plate 328 and disposed at a position at which the operating mode selector switch 138 is provided on the accumulator machine 100. Furthermore, a covering 338 is provided at the position at which the power/speed push-button 136 is provided on the accumulator machine 100, so that the plates 128 and 328 are substantially identical. The plate 328 with the power/speed push-button 326 forms a push-button unit 340. A rim 342 of the plate 328 is sealed off in a germ-proof manner by a seal, not shown, in relation to the rim 344 of the opening 326. A stop plate 346 corresponding to the stop plate 126 at the lower end of the opening 326 limits movement of the plate 328 towards the housing 302.

The drive unit 320 pushed into the motor mount 306 can be fixed with an attachment screw 366 corresponding to the attachment screw 166. For this purpose, the attachment screw 366 has an externally threaded section 368 and a head 370, which serves as stop for a rear end 374 of the motor mount 306 and is sealed off with a sealing ring 372 in relation to the rear end 374 for germ-free closure of an opening 375 provided in the rear end 374.

Protruding from the motor housing 322 in the direction towards the grip 308 is a contact block 392, from which, in turn, three motor contacts 394 identical to the motor contacts 194 protrude parallel to the longitudinal axis 396 in the form of gold-plated contact pins in the direction towards the grip 308.

A rotor 350 is part of the drive unit 320 and is removable from the latter when a gear block 362, which is fixable to the plate 328, thereby embracing the cylindrical section 324, is removed from the plate 328. The rotor 350 is substantially identical in design to the rotor 150 and comprises a bearing shaft 352, and a cylindrical permanent magnet 358 mounted on the bearing shaft 352 and having a borehole 359 which corresponds to the bearing shaft 352. A ball bearing 354 in the form of a ring bearing is fixed to an end of the bearing shaft 352 that faces in the direction towards the rear end 374. Provided in front of and behind the permanent magnet 358 are collar-like clamping elements 400 and 402, which, on the one hand, form a corrosion protection together with a thin, sleeve-like rotor armoring 364 made of amagnetic material, and, on the other hand, hold the permanent magnet 358 on the bearing shaft 352. A front end of the bearing shaft 352 forms a coupling piece 360, which has a cutout 361 disposed transversely to the longitudinal axis 304, in which a clamping member 363 is inserted, which is pushable into a groove of a drive wheel 404 of the gear block 362 and serves as catch for the drive wheel 404.

At the front end of the gear block 362 there is provided coaxially with the longitudinal axis 304 a tool receptacle 388, into which, for example, a saw blade is insertable and fixable with a screw 406.

Figure 5A:
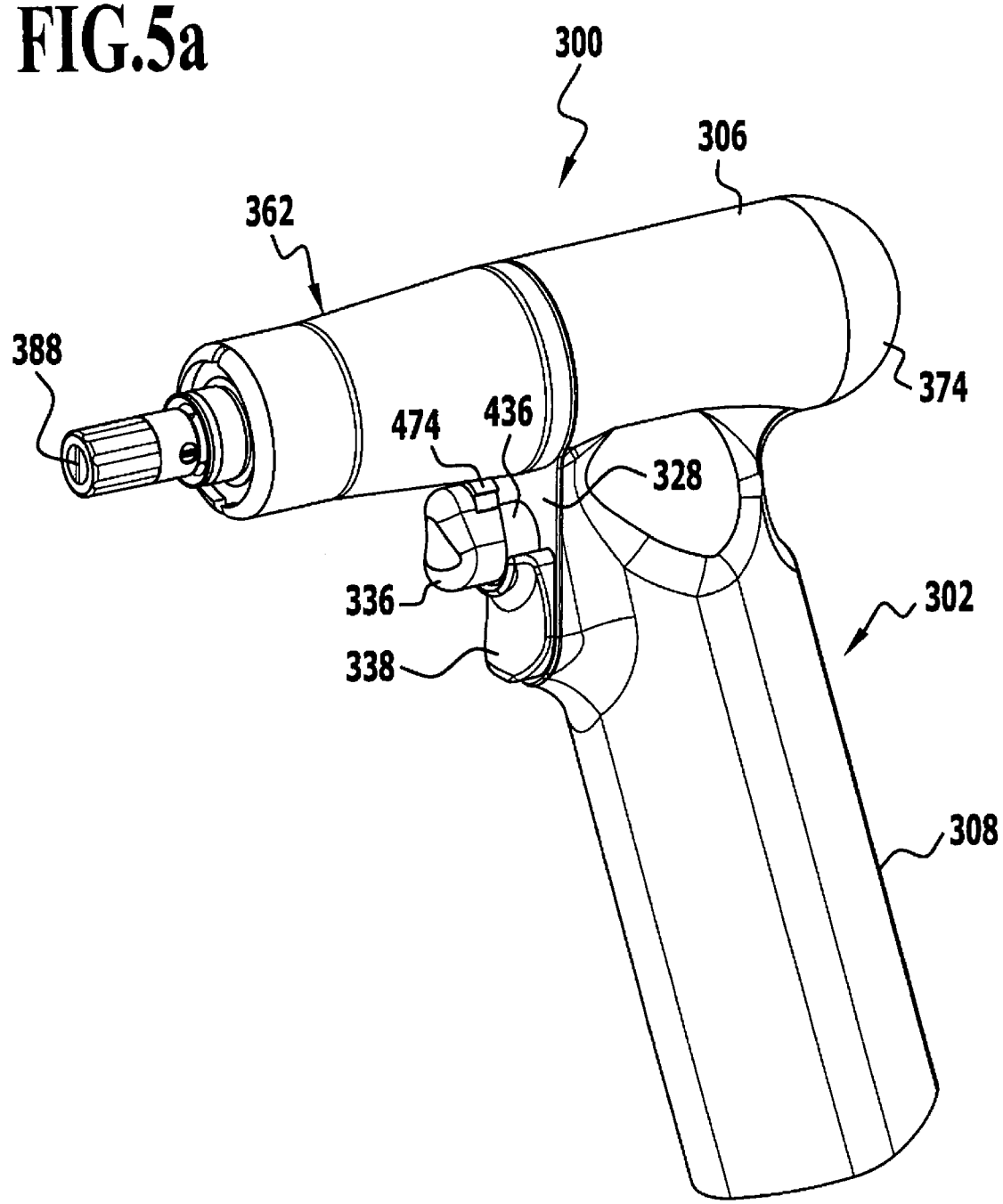
FIG. 5a a perspective view of a second embodiment of a surgical machine.
Figure 5B:
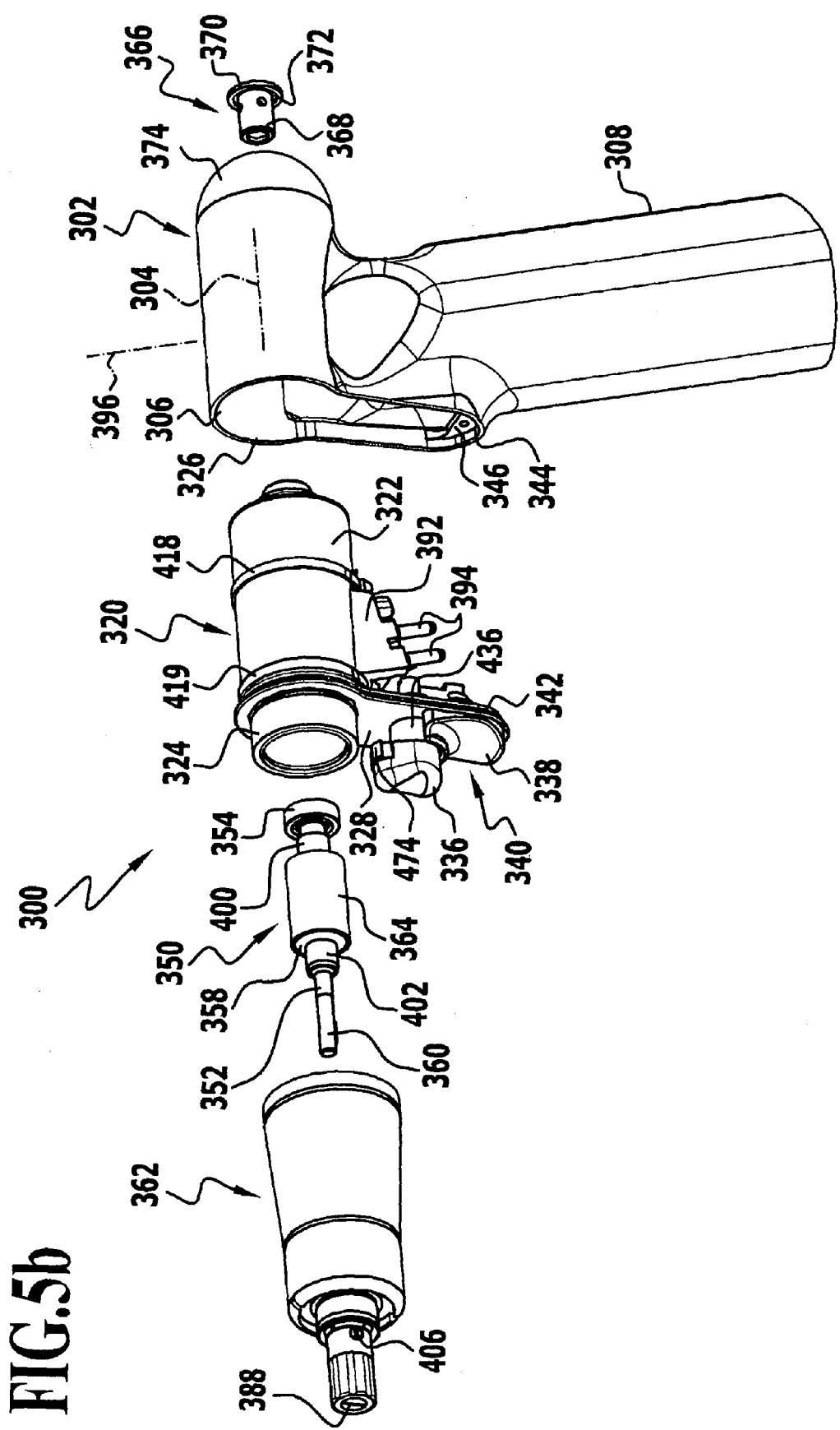
Figure 6:
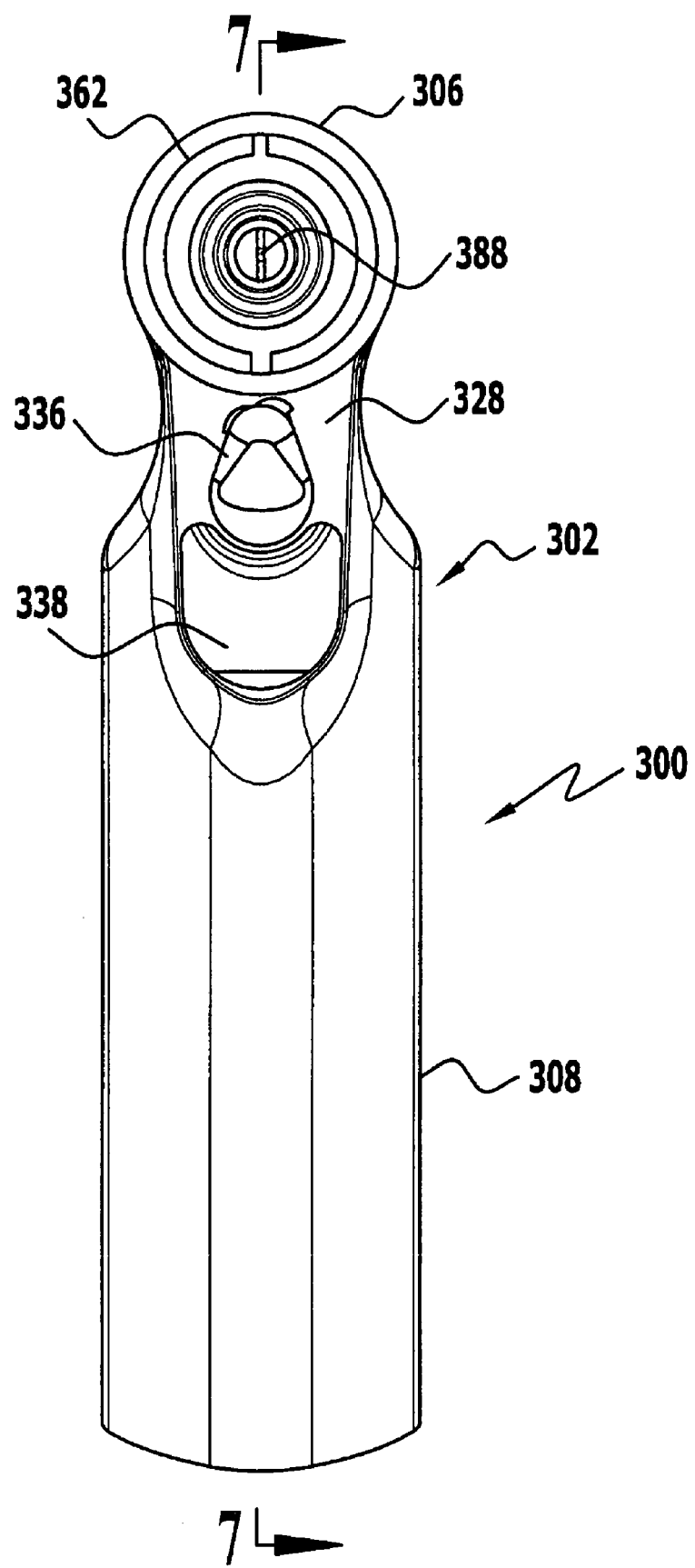
Figure 7:
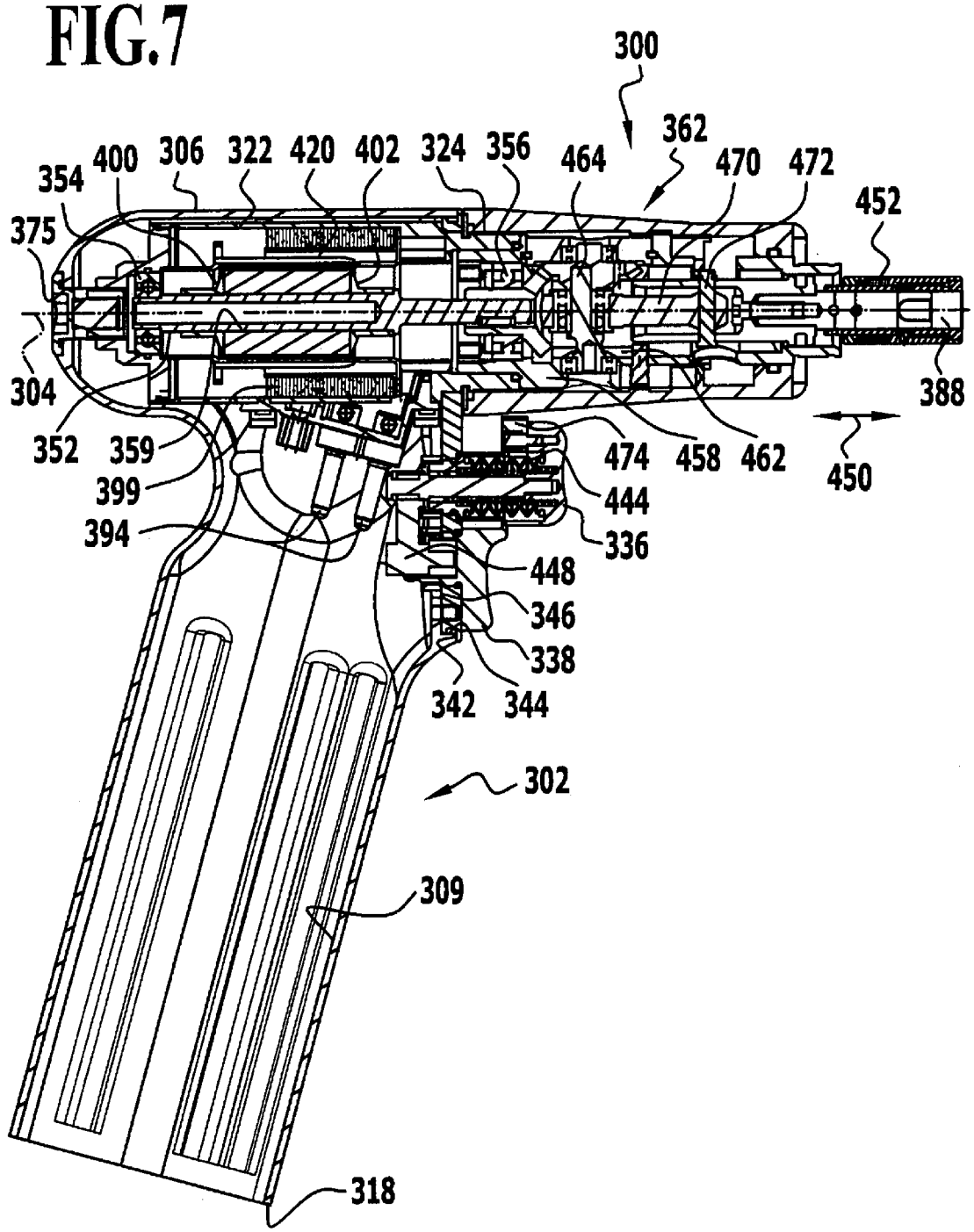
FIG. 7 a sectional view taken along line 7-7 in FIG. 6.
Figure 8:
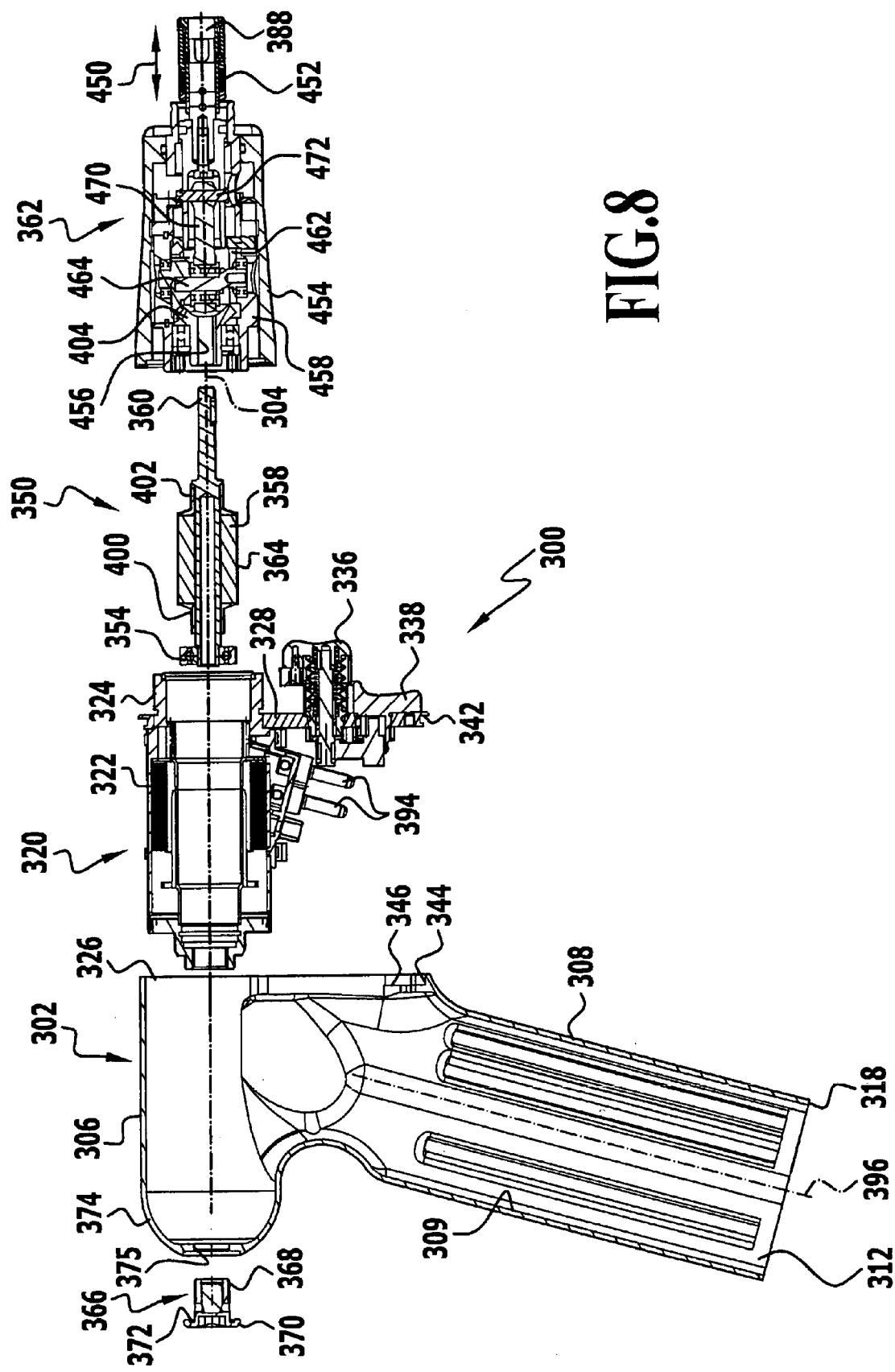
FIG. 8 a sectional view similar to FIG. 7 of the machine disassembled in FIG. 5b.
Figure 8A:
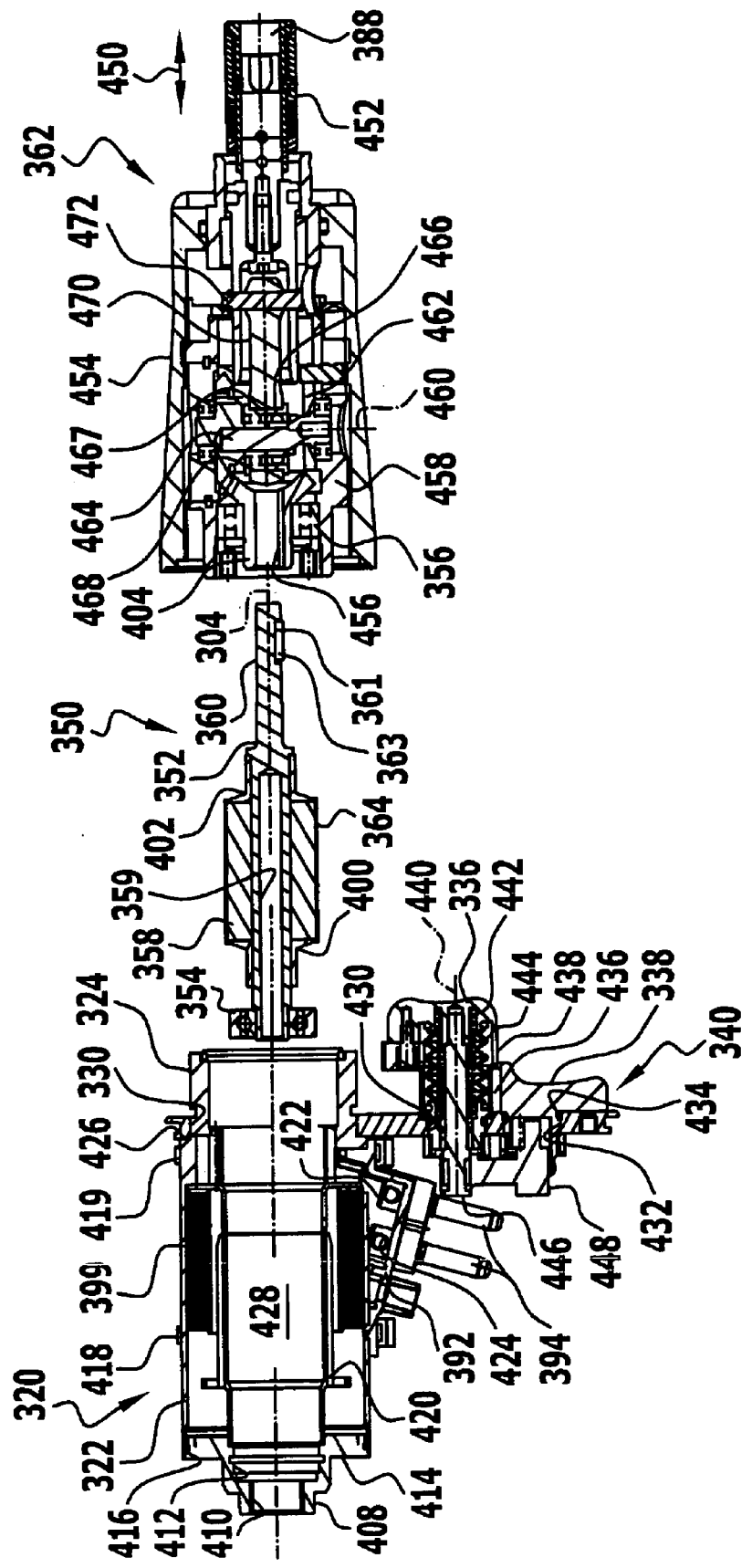
FIG. 8a an enlarged view of component assemblies shown on the right in FIG. 8.
Figure 9:
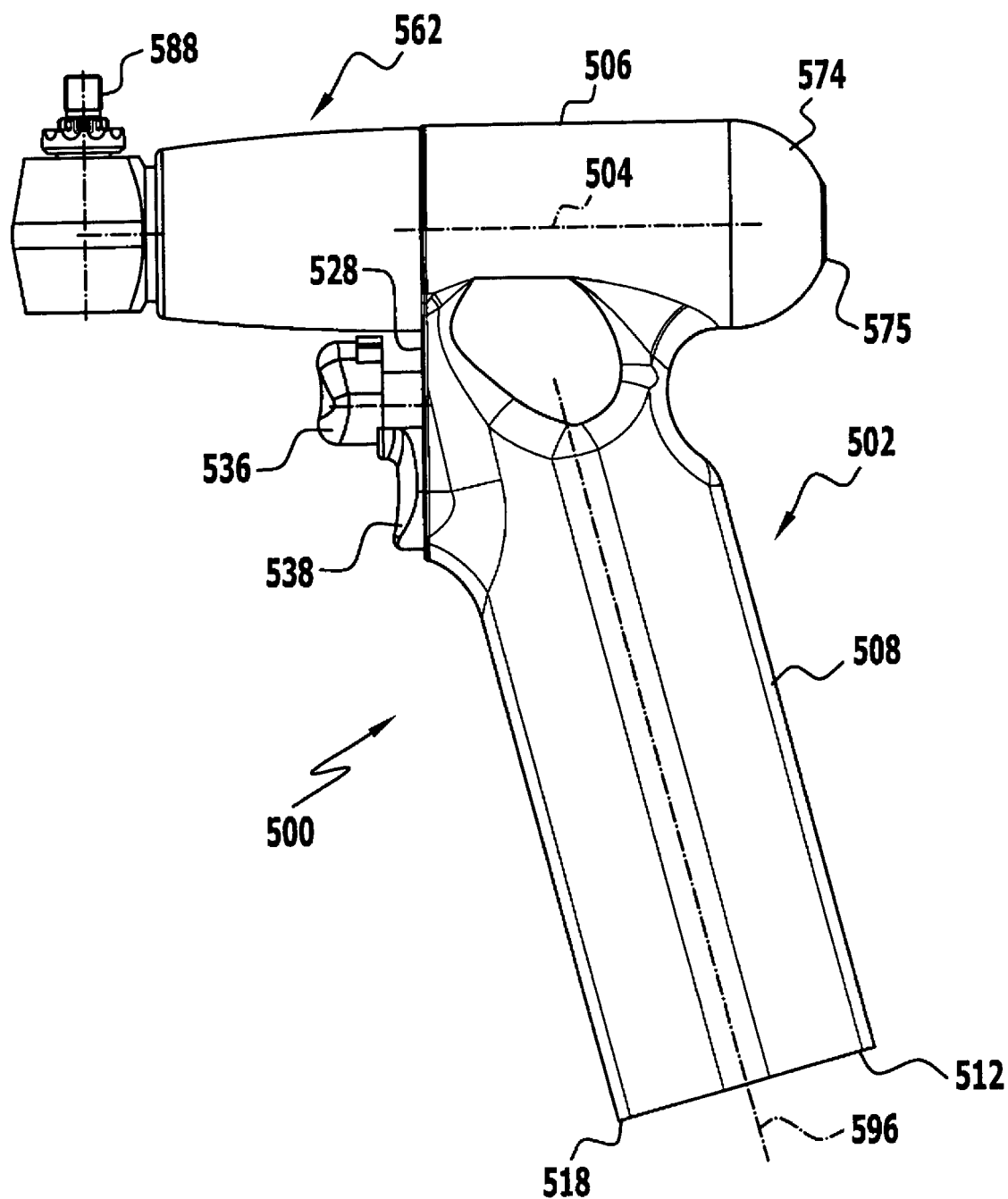
FIG. 9 a side view of a third embodiment of a surgical machine.
Figure 10:
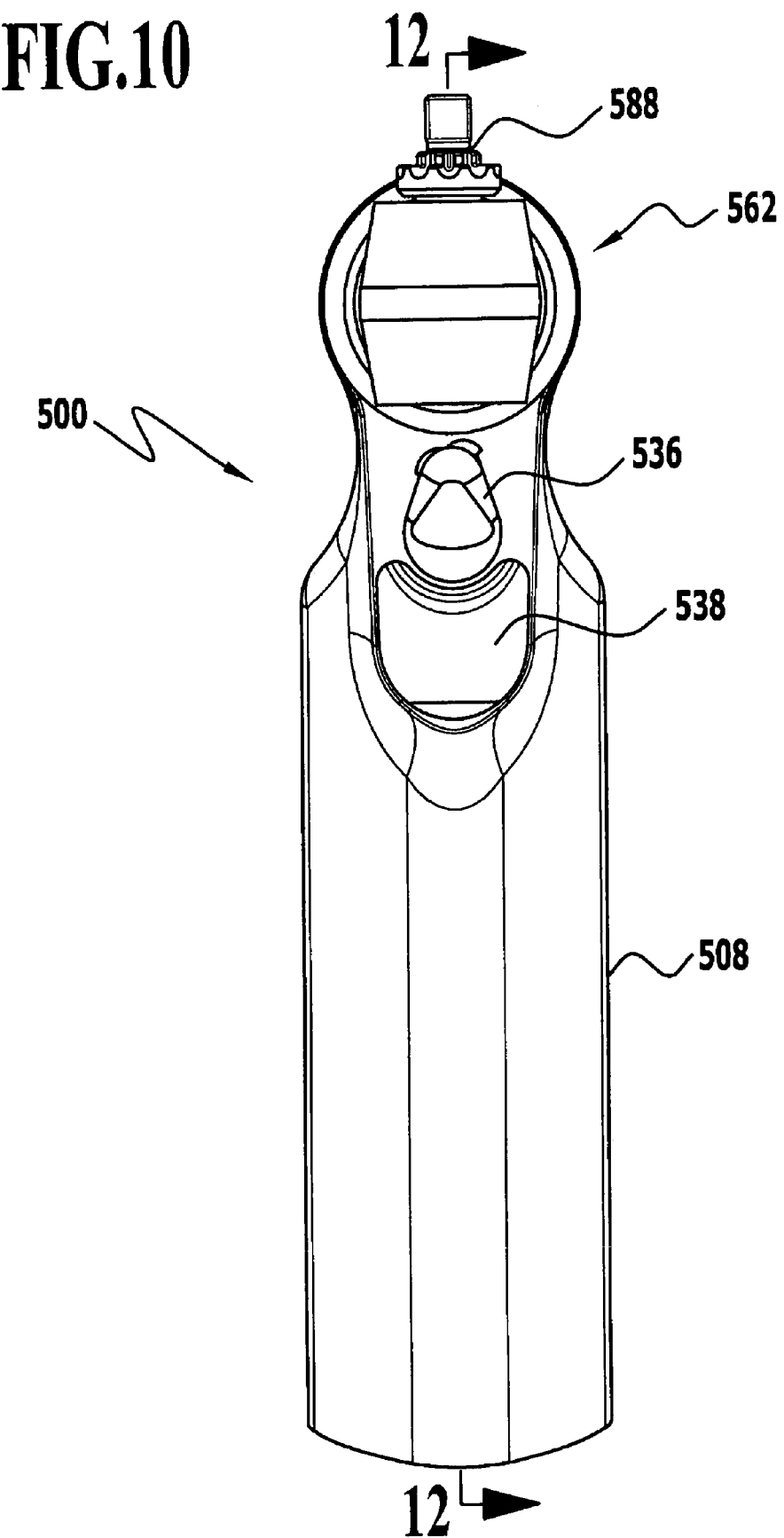
FIG. 10 a front end view of the machine shown in FIG. 9.
Figure 11:
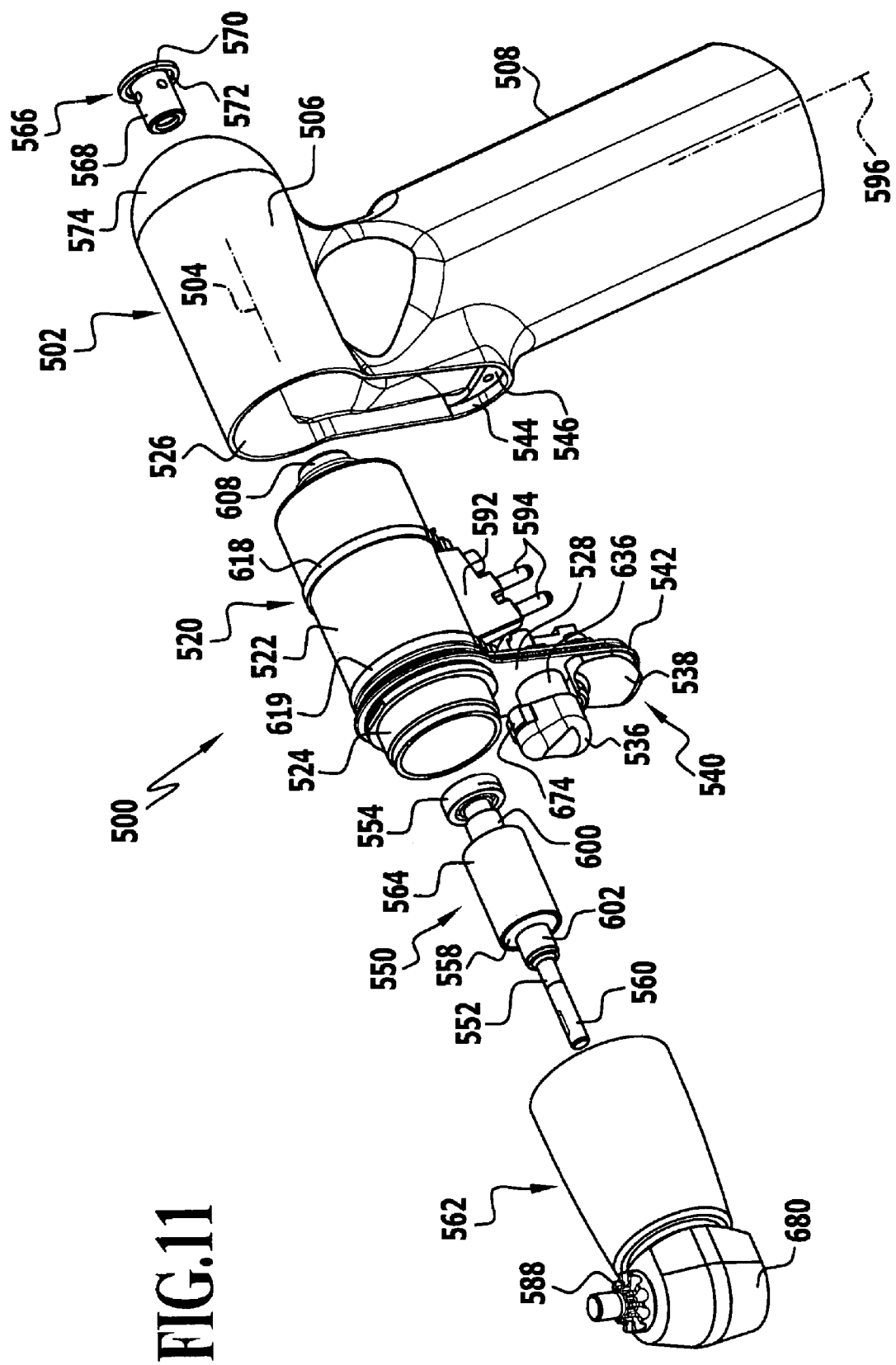
FIG. 11 an exploded representation of the machine shown in FIG. 9.
Figure 12:
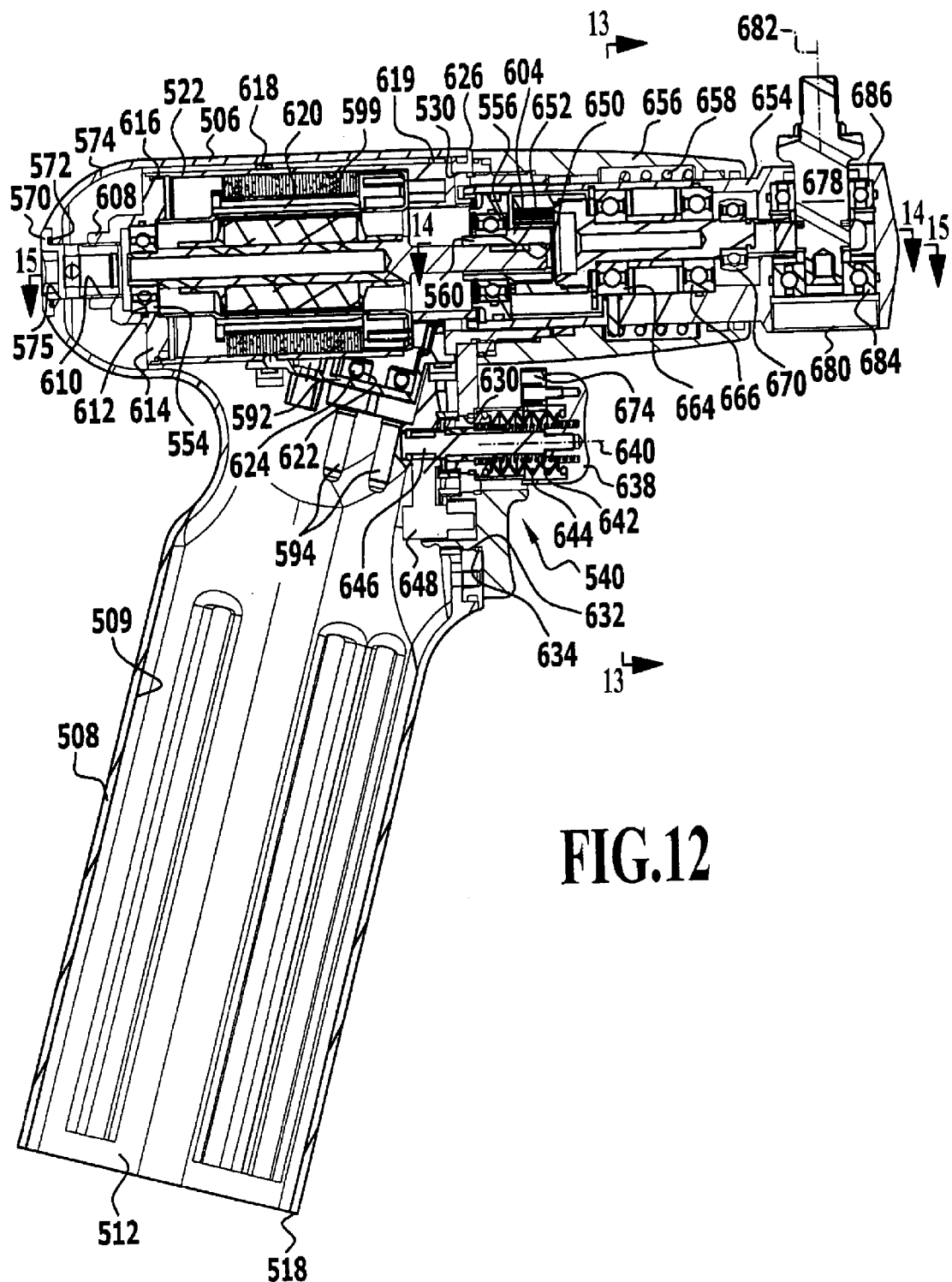
FIG. 12 a sectional view taken along line 12-12 in FIG. 10.
Figure 13:
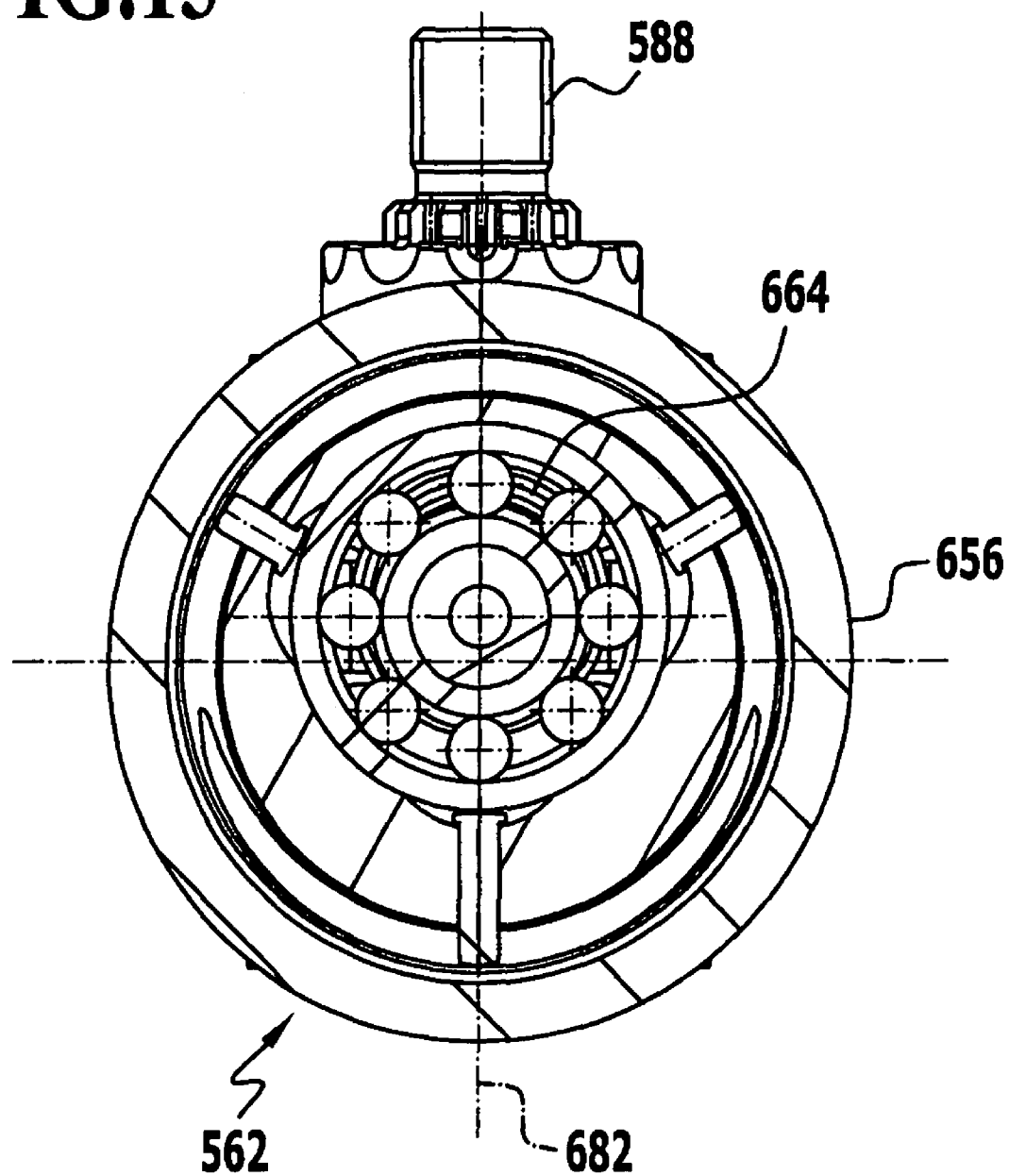
FIG. 13 a sectional view taken along line 13-13 in FIG. 12.
Figure 14:
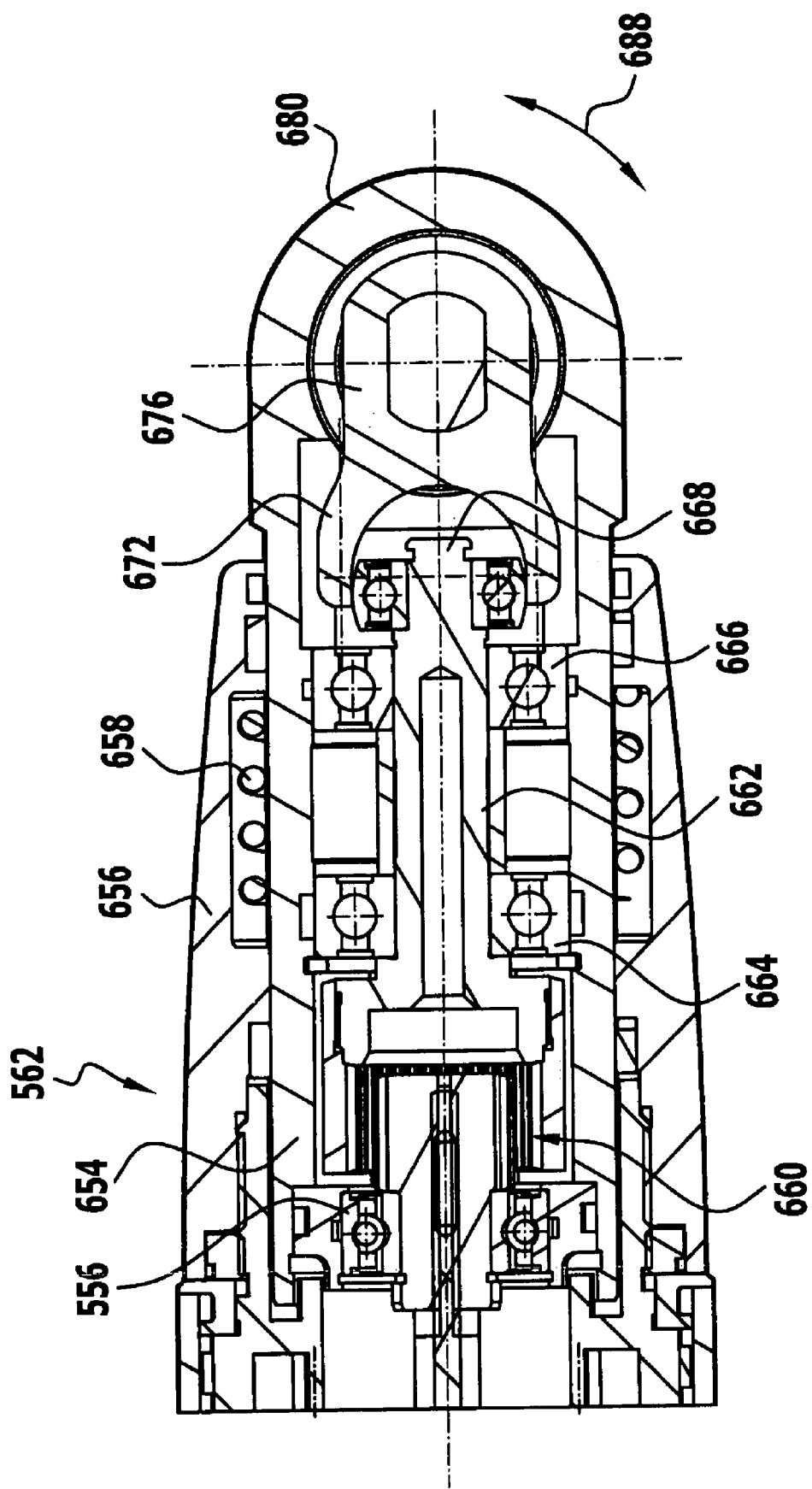
FIG. 14 a sectional view taken along line 14-14 in FIG. 12.
Figure 15:
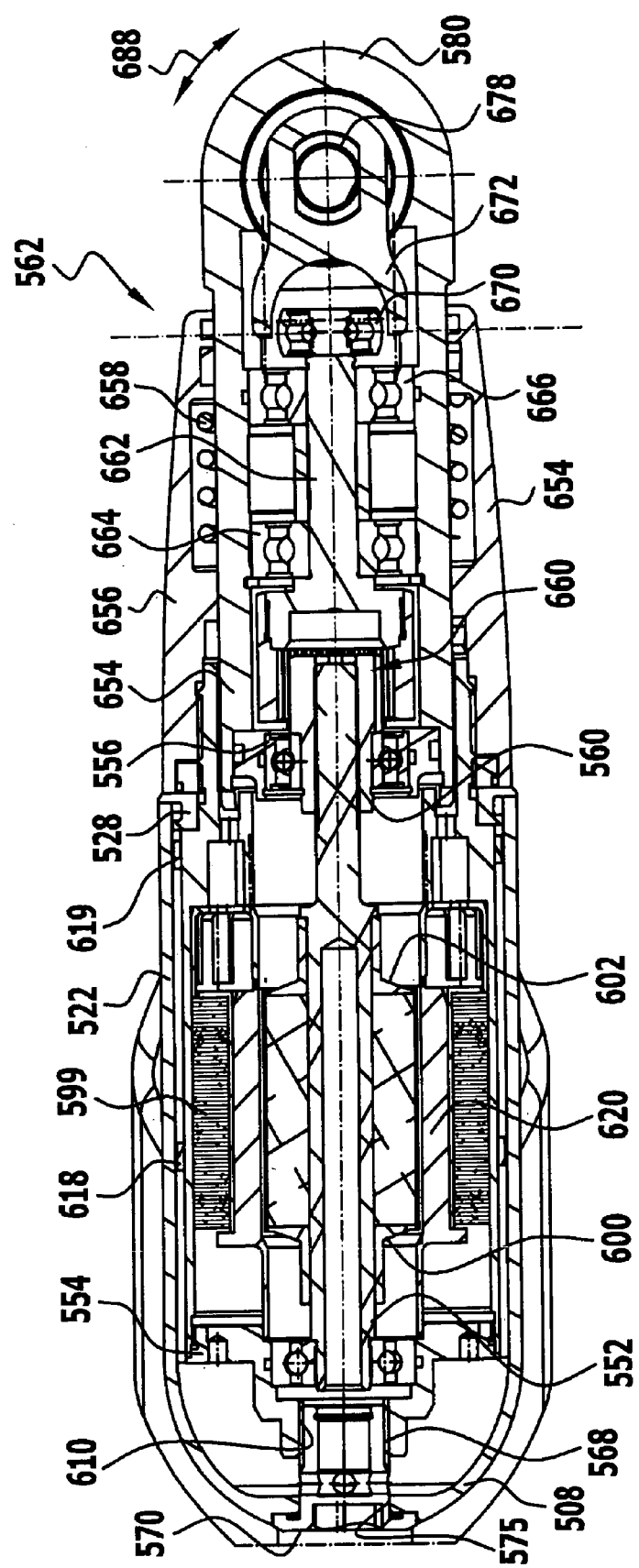
FIG. 15 a sectional view taken along line 15-15 in FIG. 12.
Figure 16:
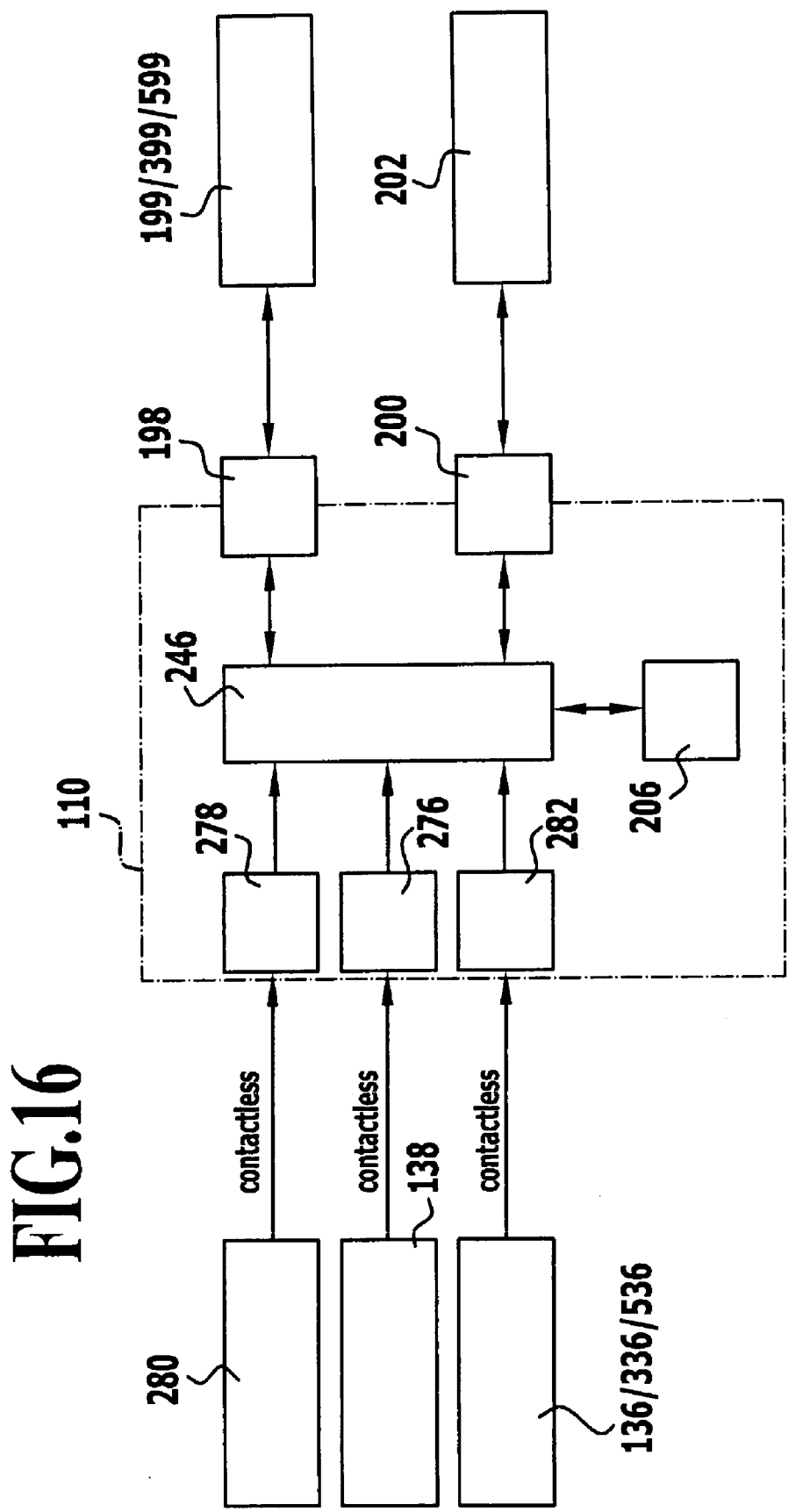
FIG. 16 a circuit diagram of a surgical machine.

An internal design of the components and component assemblies of the jigsaw 300 described in FIGS. 5a and 5b will be explained in more detail hereinbelow with reference to FIGS. 7, 8 and 8a.

A receiving space 309, which is formed in the grip 308, and into which the power and control unit 110 is insertable, is, as mentioned hereinabove, closable with a cover corresponding to the cover 114, and the circumferential seal 116 placed in the cover 114 presses against a lower rim 318 of the housing 302 and thereby closes it in a germ-proof manner. The housing has a total of three openings, namely an opening 312 for insertion of the power and control unit 110 into the grip 308, the opening 375 in the rear end 374 of the motor mount 306 for placement of the attachment screw 366 and the opening 326 for insertion of the drive unit 320 into the housing 302. Closure elements for the openings are thus formed by the attachment screw 366, the cover 114, not shown, and the plate 328. Sealing elements are respectively provided for sealing the openings 312, 374 and 326 with the closure elements described hereinabove in a germ-free manner, and for preparing the jigsaw 300, like the accumulator machine 100, after insertion of the non-sterile power and control unit 110, for use in a sterile area, for example, an operating theater.

Disposed at the rear end of the drive unit 320 is a sleeve-shaped connecting piece 408, which has an internal thread 410, which corresponds in design to the external thread of the externally threaded section 368. The connecting piece 408 expands twice, with a single step in each case, and the second expansion 412 serves to receive the ball bearing 354. The expansion 412 is followed by a radially outwardly protruding ring flange 414, which is inserted into a rear end of the motor housing 322 and is sealed off with a ring seal 416. Provided on the outside of the motor housing 322 and thereby surrounding the motor housing 322 are two spacer rings 418 and 419, which rest against the inside of the motor mount 306 when the drive unit 320 is inserted. They are preferably made of a damping material. They further serve to hold the contact block 392 on the bottom of the motor housing 322.

Inserted coaxially with the longitudinal axis 304 into the motor housing 322 is a sleeve-like winding member, onto which three motor windings 399 are wound. An end of the motor contacts 394 extending into the motor housing 322 is provided with a transverse bore 424, through which the motor windings are led and soldered. A connection area of the motor windings 399 can, therefore, be kept very short by the threading-through. The front portion 324 of the motor housing 322 extends through a borehole 330 provided for that purpose in the plate 328. A ring-shaped stop 426 on the motor housing 322, formed by a single-step reduction in the external diameter in the transition to the portion 324, abuts directly on the plate 328.

All electrically conductive elements of the motor housing 322 are fully encapsulated by casting, in particular, the motor windings 399 disposed between the winding member 420 and the motor housing 322, and the motor contacts 394 held in the contact block 392. A rotationally symmetrical receiving space 428 in the interior of the drive unit 320 serves to receive the rotor 350 described in detail hereinabove.

Two boreholes 430 and 432 are provided one over the other parallel to the longitudinal axis 304 on the plate 328 for receiving the power/speed push-button 336 and the covering 338. The covering 338 inserted in the borehole 432 is sealed off in a germ-proof manner with a ring seal 434 in relation to the plate 328. The covering 338 has on the outside an ergonomically shaped outer surface, on which an operator can preferably support his middle finger and/or ring finger.

The power/speed push-button 336 comprises a sleeve-shaped, fixed bearing member 436, which is led through the borehole 430, and on which there is provided for movement coaxially with a longitudinal axis 440 of the borehole 430 a push-button element 438, which is held by a helical spring 442 in a basic position protruding from the plate 328. A bellows seal 444 fixed, on the one hand, on the bearing member 436 and, on the other hand, on the push-button element 438, ensures a germ-free sealing of the power/speed push-button 336 relative to the plate 328.

The push-button element 438 has a pin extending through the borehole 430. At the end of the pin that extends into the housing 302 there protrudes downwards a small plate 448 having such a width that it can be pushed into the gap 268 of the power and control unit 110. It serves to actuate the Hall sensor 264 of the rotational speed prescribing sensor 282 of the power and control unit 110. In the jigsaw 300, the small soft iron plate 448 extends so far downwards that it can enter the gap 268 at the same position as a small iron plate, not shown in the Figures, which is disposed on the power/speed push-button 136 of the accumulator machine 100. Owing to the special shape of the small soft iron plate 448, there is no necessity for any changes to the power and control unit 110 so as to be able to operate it with both the accumulator machine 100 and the jigsaw 300, although the power/speed push-button 336 is disposed at the position on the jigsaw 300 at which the operating mode selector switch 138 is provided on the accumulator machine 100. This exchanged arrangement of the power/speed pushbuttons 136 and 336, respectively, has the advantage that, ergonomically, operation of both the accumulator machine 100 and the jigsaw 300 is particularly convenient.

Where the plate 328 is connected to the housing 302, the power/speed push-button 136 and the operating mode selector switch 138 and also the power/speed push-button 336 can be removed from the plate 328 for maintenance purposes.

The motor windings 399 wound onto the winding member 420 are cast in a cold casting process under vacuum or under normal atmosphere with epoxy resin, so that no cavities arise in which germs can settle owing to the open construction of both accumulator machine 100 and jigsaw 300. Furthermore, the casting serves as protection against vibrations and as protection against hot steam during sterilization of the machines. The cold casting substance can be advantageously filled with fillers, which improve heat transfer away from the motor windings 399.

The drive unit 320 thus comprises a three-phase electronically commutated motor, which is of identical design and sensorless in all embodiments, i.e., in particular, no Hall system with Hall sensors is present for gaining knowledge of a position or orientation of the rotor 350, which is necessary for supplying the motor windings 399 with current. A rotor position is determined by a sensorless method, as will be explained hereinbelow. In principle, it is, however, also conceivable to provide sensors for detecting a rotor position in the drive unit 320.

The gear block 362 serves to convert a rotation of the rotor 350 into an oscillating movement, indicated by arrow 450, coaxially with the longitudinal axis 304, of a coupling part 452 having a coupling receptacle 388 for receiving a saw blade. The gear block 362 has a substantially conical housing, in the rear end of which a drive wheel 404, mounted by the ball bearing 356, is mounted. The coupling piece 360 of the rotor 350 is insertable into the cylindrical receptacle 456 of the drive wheel 404. The ball bearing 356 is held in a bearing member 458, which extends further in the direction towards the front end of the gear block 362. Mounted about a longitudinal axis 460 transversely to the longitudinal axis 304 on the bearing member 458 is a drive wheel 462, which is driven by the drive wheel 404. The drive wheels 404 and 462 can be configured either as cylindrical gear and gear wheel or as two bevel gears. Eccentrically in relation to the longitudinal axis 460, the drive wheel 462 carries parallel to the longitudinal axis 460 a connecting rod 464, on which two ball bearings 466 and 467 are mounted, which are held in a borehole 468 of a drive rod 470 arranged coaxially with the longitudinal axis 304. The coupling part 452 is connected by a shaft 472 to the connecting rod 464, so that as a result of a rotation of the drive wheel 462, the connecting rod 464 moves the drive rod 470 periodically, and the drive rod 470 moves the shaft 472 back and forth, as indicated by arrow 450, parallel to the coupling part 452, which is mounted by means of slide bearings in the housing 454.

The gear block 362 is connected by a quick-acting closure to the front portion 324 of the motor housing 322. If the gear block 362 is removed, the rotor 350 can be removed from the drive unit 320 without the latter having to be taken out of the housing 302.

The drive wheels 404 and 462 form a reduction stage, so that the motor can be operated in a range with higher efficiency, for which the power and control unit 110 has only to provide a relatively low motor current for a high rotational speed of the motor to be achievable. As a result, when loaded with a saw, the rotational speed of the motor does not drop to a range below the power maximum of the motor, but nevertheless the motor current does not rise sharply. In spite of additional frictional losses and losses owing to the higher rotational speed of the motor, the reduction stage is positive for the power balance of the machine, in other words, the machine can be operated longer with the same power made available by the power and control unit 110. The operating time of the machine does, however, depend strongly on the amount of motor current withdrawn.

A pivotably mounted locking element 474 is provided on the power/speed push-button 336, as also on the power/speed push-button 136. It is mounted on the push-button element 438 for pivotal movement about an axis parallel to the longitudinal axis 440. In a first extreme pivot position, it allows movement of the push-button element 438 parallel to the longitudinal axis 440, in another extreme pivot position, movement of the push-button element 438 in the direction towards the plate 328 is locked. The locking element 474 thus serves to secure the machine against unintentional operation thereof.

A third embodiment of a surgical machine according to the invention in the form of an oscillating saw, generally designated by reference numeral 500, is shown in FIGS. 9 to 15. The design of the saw 500 corresponds substantially to that of the jigsaw 300, so that identical parts or components are designated by reference numerals between 500 and 699, which are used in analogy with the reference numerals 300 to 499 used to describe the jigsaw 300.

The power and control unit 110 comprising the motor controller 246 serves as power supply. The power and control unit 110 can be pushed into a receiving space 509 of a grip 508 of a housing 502 and secured by closing the opening 512 with a cover corresponding to the cover 114. The grip 508 protrudes substantially transversely from a motor mount 506, which defines a longitudinal axis 504. The cover for closing the opening 512 has a seal, which presses against a lower rim of the grip 518 and thereby closes the receiving space 509 in a germ-proof manner.

A drive unit 520 is mounted on a plate 528 and comprises a motor housing 522, from which a contact block 592, additionally secured with spacer rings 618 and 619, protrudes in the direction towards the grip 508. The contact block 592 carries three pin-like motor contacts 594, which protrude parallel to the longitudinal axis 596 and are conductively connected to three motor windings 599.

Two boreholes 630 and 632 disposed one above the other on the plate 528 and orientated parallel to the longitudinal axis 504 serve to receive a power/speed push-button 536 and a covering 538, respectively, which together with the plate 528 form a push-button unit 540. A substantially keyhole-like opening of the housing 502 in the area of the motor mount 506 and in the area of transition to the grip 508 serves for insertion of the drive unit 520 into the housing 502. A rim 542 of the plate is sealed off in relation to a rim 544 of the opening 526 by a seal, not shown. In order that the plate 528 is held in a defined position, a stop plate 546 is provided in the lower area of the opening 526.

The drive unit 520 inserted into the housing 502 is secured by an attachment screw 566 with an externally threaded section 568 being screwed to an internal thread 610 of a connection piece 608 at the rear end of the drive unit 520. For this purpose, there is provided at the rear end 574 of the motor mount 506 an opening 575, at the rim of which a head 570 of the attachment screw 566 is supported. By means of a seal 572 between the head 570 and the rim of the opening 575, the latter is sealed in a germ-proof manner.

A sleeve-shaped portion 524 at the front end of the drive unit 520 extends through a borehole 530 of the plate 528 and is connectable to a gear block 562, which carries at its front end an angular part 680, which is provided with a peg-shaped tool receptacle 588, on which, for example, a saw blade with a corresponding borehole can be placed and secured.

If the gear block 562 is removed from the plate 528, a rotor 550 can be removed from the drive unit 520. The rotor comprises a substantially cylindrical bearing shaft 552, to the rear end of which a ball bearing 554 is fixed. A cylindrical permanent magnet 558 with a borehole extending in the direction of the longitudinal axis 504 is positioned on the bearing shaft 552 and simultaneously protected and held in circumferential direction by a thin, sleeve-like rotor armoring and at its end faces by collar-like clamping elements 600 and 602. A front end of the bearing shaft 552 forms a coupling piece 560, which is engageable in a rotationally fixed manner with a drive wheel 604.

An internal design of the saw 500, in particular, of the gear block 562, will be explained in more detail hereinbelow with reference to FIGS. 12 to 15.

The connection piece 608 expands twice in a single step in the internal diameter, and the ball bearing 554 is held in the area of its second expansion 612. A ring flange 614 protruding radially outwardly from the connection piece 608 serves in conjunction with a ring seal 616 to close a rear end of the motor housing 522. Inserted into the motor housing 522 is a winding member 620, onto which the motor windings 599 are wound. As described in conjunction with the design of the jigsaw 300, the motor windings 599 are also fully encapsulated by cold casting. In the contact block 592, ends 622 of the motor contacts 594 pointing towards the longitudinal axis are provided with transverse boreholes 624, through which the motor windings 599 are threaded and soldered. A ring-shaped stop 626 in the area of transition of the motor housing 522 in the front portion 527 abuts directly on the plate 528.

The push-button unit 540 is identical in design to the push-button unit 340. The power/speed push-button 536 comprises a bearing member 636, which is inserted into the bore 630 and is sealed off in a germ-proof manner in relation to the plate 528. The ergonomically shaped covering 538 for supporting a middle or ring finger is sealed off in relation to the plate 528 by a ring seal surrounding the borehole 632. A push-button element 638 is mounted in the bearing member 636 for displacement coaxially with a longitudinal axis 640. The push-button element, when it is not actuated, is held by a helical spring 642 in a basic position in which it projects maximally from the plate 528. A bellows seal 644 secured, on the one hand, on the bearing member 636 and, on the other hand, on the push-button element 638 serves to seal the power/speed push-button 536 relative to the plate 528. The push-button element 638 comprising a pin 646 extending into the housing 502 carries at the protruding end of the pin 646 a downwardly facing small soft iron plate 648 having dimensions that enable it to be pushed into the gap 268 of the power and control unit 110. By actuating the power/speed push-button 536 the rotational speed prescribing sensor 282 is actuated, whereupon the motor controller 246 acts upon the drive unit 220 with a current that is required for the desired rotational speed.

The gear block 562 has at its rear end facing towards the plate 528 a receptacle 650 for the coupling piece 560. Provided on the latter is a cutout 652 into which a projection in the receptacle 650 can enter, whereby a rotationally fixed connection is established between the drive wheel 604 and the bearing shaft 552. The drive wheel 604 is mounted by means of the ball bearing 556 on an inner part of the housing. The inner part of the housing is mounted for rotation about the longitudinal axis 504 relative to an outer housing 656 and is held by a helical spring in a basic position in which the gear block 562 is locked on the plate 528.

The drive wheel 604 is part of a reduction unit 660, with which a rotational speed of the drive unit 520 can be reduced to a desired value. A drive shaft 662, mounted by means of two ball bearings 664 and 666 in the inner part 654 of the housing, parallel to, but offset somewhat from the longitudinal axis 504, is driven by the reduction unit 660. A front end of the drive shaft 662 is in the form of an eccentric pin 668, which carries a ball bearing 670 with a spherical outer surface, which is held in a fork-shaped end 672 of an oscillating lever 676. The oscillating lever is fixed to a shaft 678, which is mounted in the angular piece 680 for rotation about an axis of rotation 682, and the end of which protruding from the angular piece 680 forms the tool receptacle 588. The axis of rotation 682 extends perpendicularly to the longitudinal axis 504 and intersects it. The shaft 678 is mounted by means of two ball bearings 684 and 686 in the angular piece 680. As a result of rotation of the drive shaft 662, the pin 668 executes an eccentric movement and forces an oscillating movement upon the end 672 and hence upon the oscillating lever 676, and the ball bearing 670 is able to slide in the fork-shaped end 672. The oscillating movement of the shaft 678 is indicated by an arrow 688 in FIGS. 14 and 15.

Owing to the drive shaft 662 being disposed parallel to the bearing shaft 552, a particularly small outer diameter of the outer housing 656 and a symmetrical design of the latter can be achieved. However, if an alternative reduction unit were used, the drive shaft 662 could also be disposed coaxially with the bearing shaft 552.

All three machines described herein, i. e., the accumulator machine 100, the jigsaw 300 and the oscillating saw 500 have in common that the drive units 120, 320 and 520 and the coupling device 180 and the gear blocks 362 and 562 are not sealed off. This has the advantage that these machine areas are made germ-free inwards during the sterilization. Oil can be sprayed through the above-mentioned elements for lubrication of the bearings. Alternatively, the drive units could also be sealed off, and the bearings lubricated for the entire life span. The interior could nevertheless be made germ-free by sterilization if a membrane valve as described in International Patent Application PCT/EP03/00911 were provided.

Connection possibilities for a washing machine can be additionally provided in the area of the machine drive and in the area of the machine output, so that soiled channels of rotatory drives can be manually cleaned, and likewise soiled tool receptacles 588 for saw blades.

Owing to the possibility of releasing the drive units 120, 320 and 520 from the respective housing 102, 302 and 502, it is possible to also test and operate the drive units 120, 320 and 520 outside of the housing.

It will now be explained in more detail with reference to FIGS. 16 to 19 how the power and control unit 110 functions in conjunction with the push-button units 140, 340 and 540.

The rotational speed prescribing sensor 282 of the power and control unit 110 can be contactlessly actuated with the power/speed push-buttons 136, 336 and 536. Corresponding signals arriving at the motor controller 246 from the rotational speed prescribing sensor are processed, and the motor contacts 194 and the motor windings 199, 399 and 599, respectively, connected thereto are acted upon accordingly with current via the connection contacts 198, in order to operate the drive units 120, 320 and 520 at a corresponding rotational speed. The operating mode selector switch 138 serves to contactlessly actuate the light barrier 276, which, in the event of interruption, switches the accumulator machine 100 over from clockwise operation to counterclockwise operation.

Furthermore, the light barrier 278 can be contactlessly actuated with the projection 280. If this occurs, the motor controller 246 activates or deactivates the basic possibility of switching the accumulator machine 100 over to oscillatory operation or pilgrim step operation.

Figure 17:
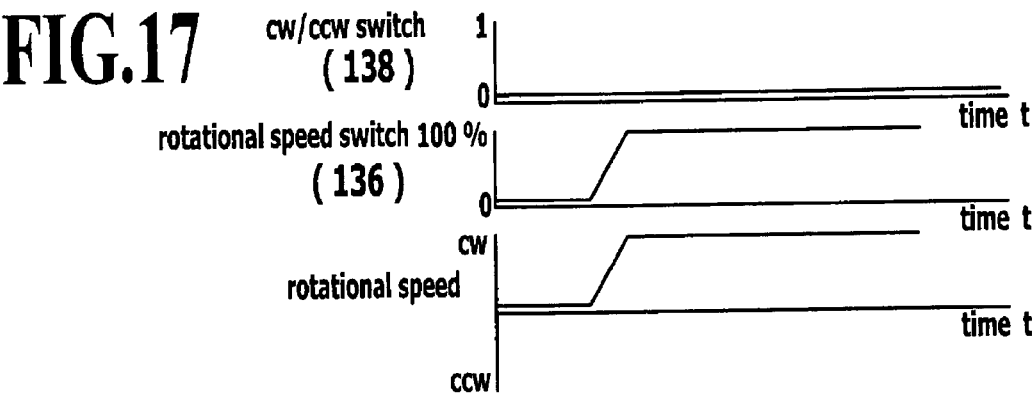
FIG. 17 a schematic representation of a time-related progression of operation of a surgical machine.

Time-related progressions of a rotational speed of the bearing shaft 152 and of a percent actuation of the power/speed push-button 136 serving as rotational speed sensor are shown in FIG. 17. The operating mode selector switch 138 serving as clockwise (cw)/counterclockwise (ccw) switch is not actuated in the time-related progressions shown in FIG. 17. The further the power/speed push-button 136 is pressed in, maximally as far as the stop, which corresponds to the value 100% in the diagram, the greater is the increase in the rotational speed of the drive unit 120.

Figure 18:
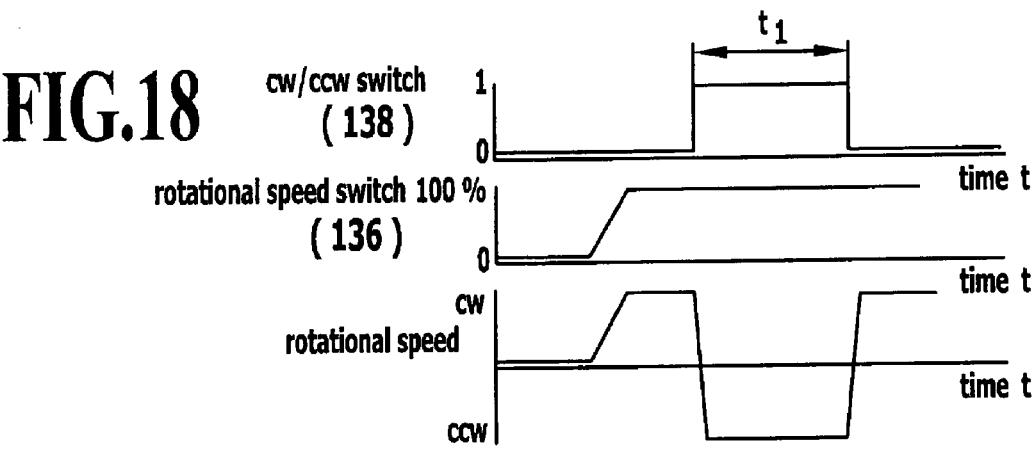
FIG. 18 a further representation of a time-related progression of operation of a surgical machine.

Differently from FIG. 17, it is shown in FIG. 18 that during operation of the accumulator machine 100 in clockwise rotation, the operating mode selector switch 138 is pressed for a time $t_1$. The consequence of this is that the drive unit switches over from clockwise operation to counterclockwise operation, which is recognizable in the time-related progression of the rotational speed.

Figure 19:
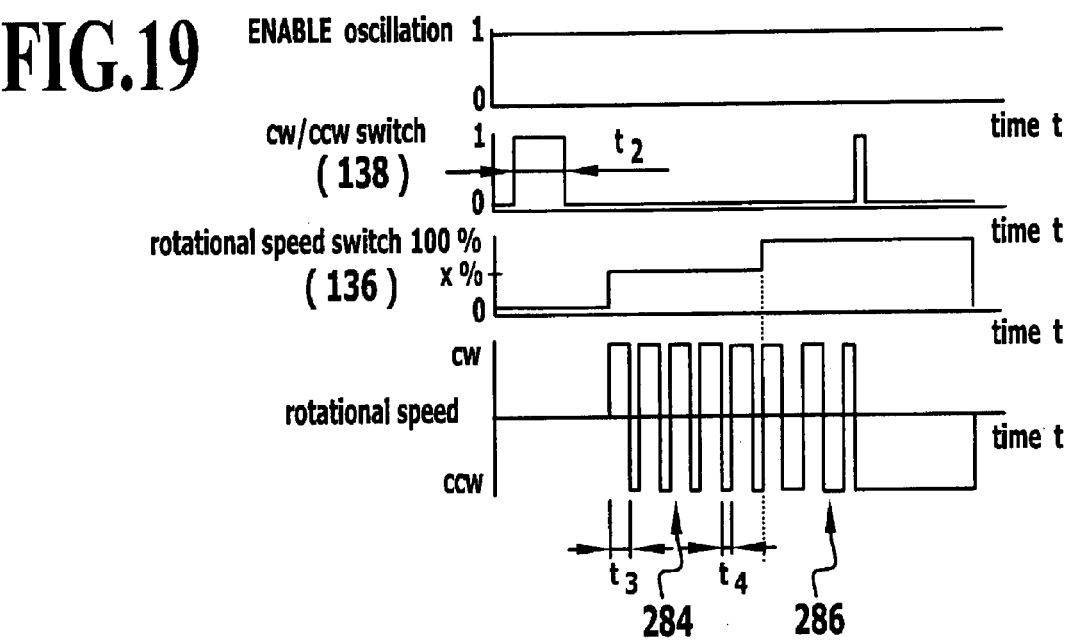
FIG. 19 a further representation of a time-related progression of operation of a surgical machine.

Provided that a corresponding signal, designated in FIG. 19 by "ENABLE oscillation", is supplied by the light barrier 278, the accumulator machine 100 can be operated not only in clockwise operation or counterclockwise operation, as described with reference to FIGS. 17 and 18, but also in oscillatory operation or in pilgrim step operation. The precondition for this is that the accumulator machine 100 first be at a standstill. If the operating mode selector switch 138 is pressed for a time $t_2$, which is greater than a prescribed switchover time, which, for example, can be prescribed in a range of one second to ten seconds, it can then be signalized, for example, by an acoustic signal generated by the power and control unit 110 that the accumulator machine 100 was switched over into the oscillatory mode. If, after the switchover, the power/speed push-button 136 is pressed only to maximally X %, then the motor controller 246 activates the drive unit 120 in the so-called pilgrim step operation, as indicated by arrow 284 in FIG. 19. Herein the drive unit periodically changes the direction of rotation, but the drive unit 120 is respectively operated during a time $t_3$ in clockwise rotation and during a time $t_4$ in counterclockwise rotation, the time $t_3$ being somewhat greater than the time $t_4$. This results in a "stuttering" clockwise rotation. Switchover to the actual oscillatory operation, indicated by arrow 286 in FIG. 19, during which the drive unit 120 is respectively operated for an equal length of time in clockwise rotation and counterclockwise rotation, only takes place when the power/speed push-button 136 is pressed more than the preset X %. If the operating mode selector switch 138 is actuated for a short time, the motor controller 246 switches the accumulator machine 100 over to counterclockwise operation. Switchover to oscillatory operation, in turn, requires continuous actuation of the operating mode selector switch 138, with the drive unit 120 at a standstill, for at least the prescribed switchover time.

The design and operation of a motor controller for a surgical machine operable in dependence upon the mains power supply or independently of the mains power supply will now be explained in more detail hereinbelow with reference to FIGS. 20 to 22.

Figure 20:
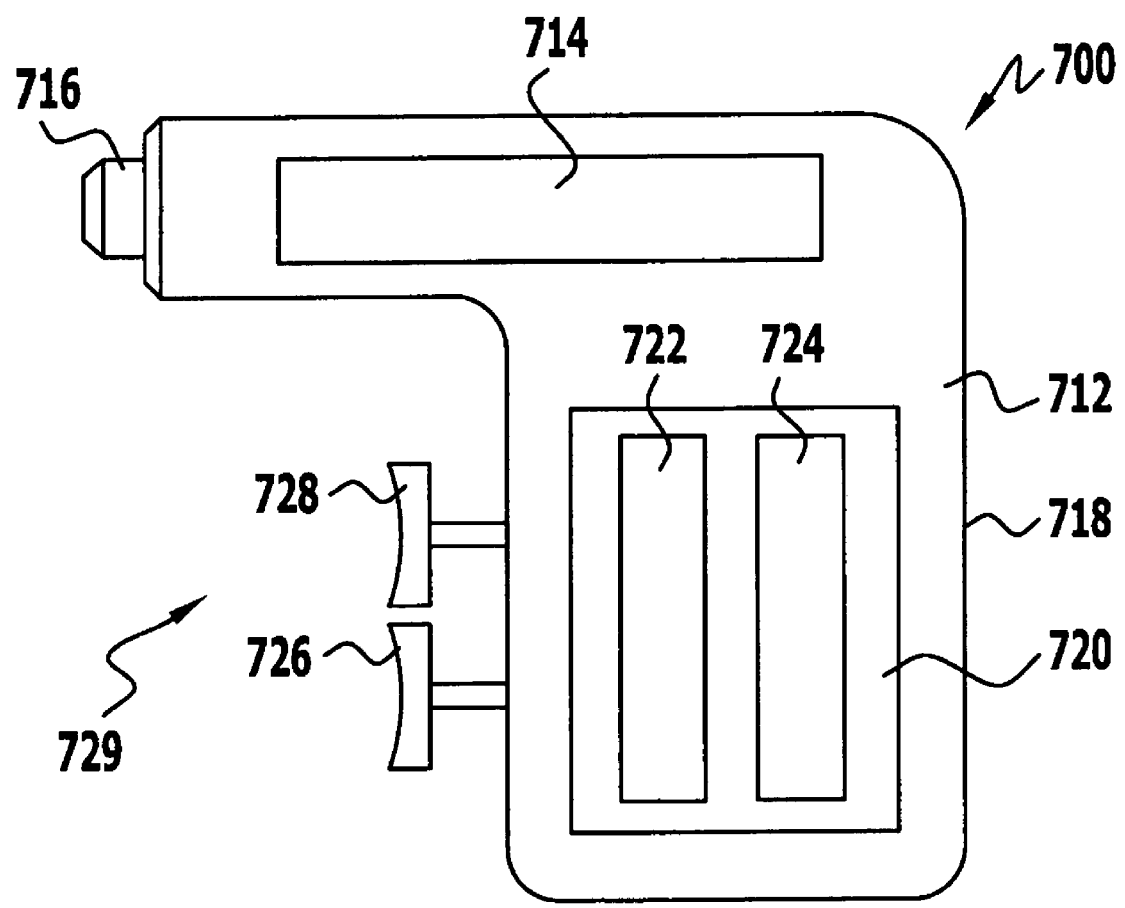
FIG. 20 a schematic representation of a surgical accumulator machine.

A surgical accumulator machine, generally designated by reference numeral 700, is shown purely schematically in FIG. 20. This can also be, for example, the above-described accumulator machine 100, the jigsaw 300 or the oscillating saw 500, which can differ in the details of their design from the accumulator machine 700. The accumulator machine 700 comprises a housing 712, in one part of which a sensorless electric motor 714 is disposed parallel to the longitudinal axis of this housing part and drives a drive shaft, not shown, of the accumulator machine 700. Disposed at the end of the drive shaft is a coupling 716, with which the accumulator machine 700 can be connected to any of kind of tool, for example, drills, mills, chisels and also saws or gear units for connection to one of the tools cited by way of example.

Protruding transversely from the housing part of the housing 712 that receives the electric motor 714 is a grip 718, into which a power and control unit in the form of a power pack 720 is insertable. The power pack 720 comprises a rechargeable battery or accumulator cell 722 and a motor controller 724. For starting the accumulator machine 700, two push-buttons, namely a power/speed push-button 726 and an operating mode selector switch 728, are provided, which can be pressed into the grip 718 substantially parallel to a longitudinal axis of the electric motor 714. The power/speed push-button 726 and the operating mode selector switch 728 together form a push-button unit.

The electric motor 714 is preferably a sensorless brushless DC motor, i. e., no rotational speed detection sensors are provided for detecting a rotor movement and a position of a rotor magnet, referred to hereinbelow as rotor, of the electric motor 714. In principle, it is, however, also conceivable to use an electric motor that is equipped with a sensor system for detection of the rotational speed.

Figure 21:
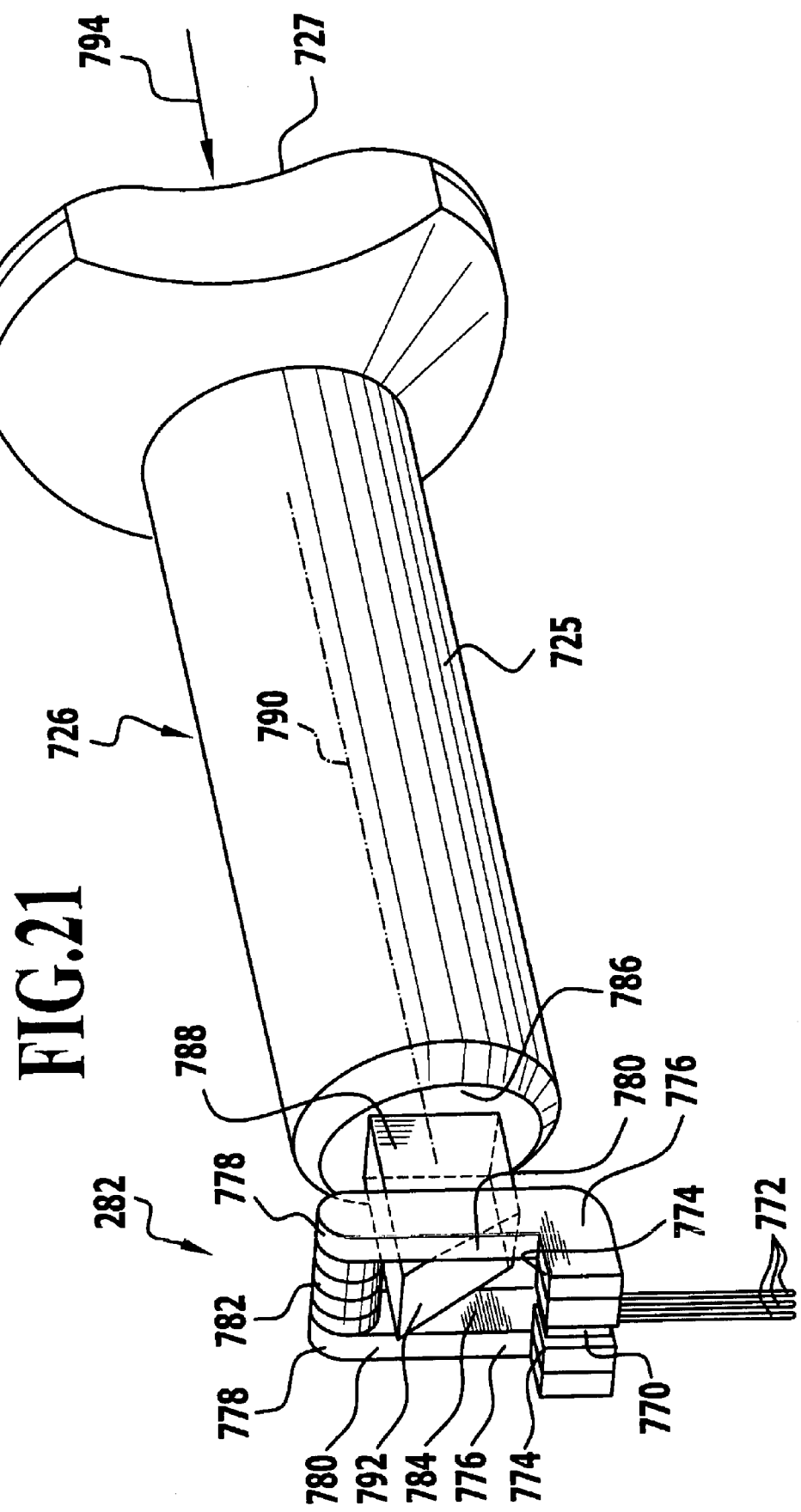
FIG. 21 a schematic representation of a push-button/sensor assembly.
Figure 22:
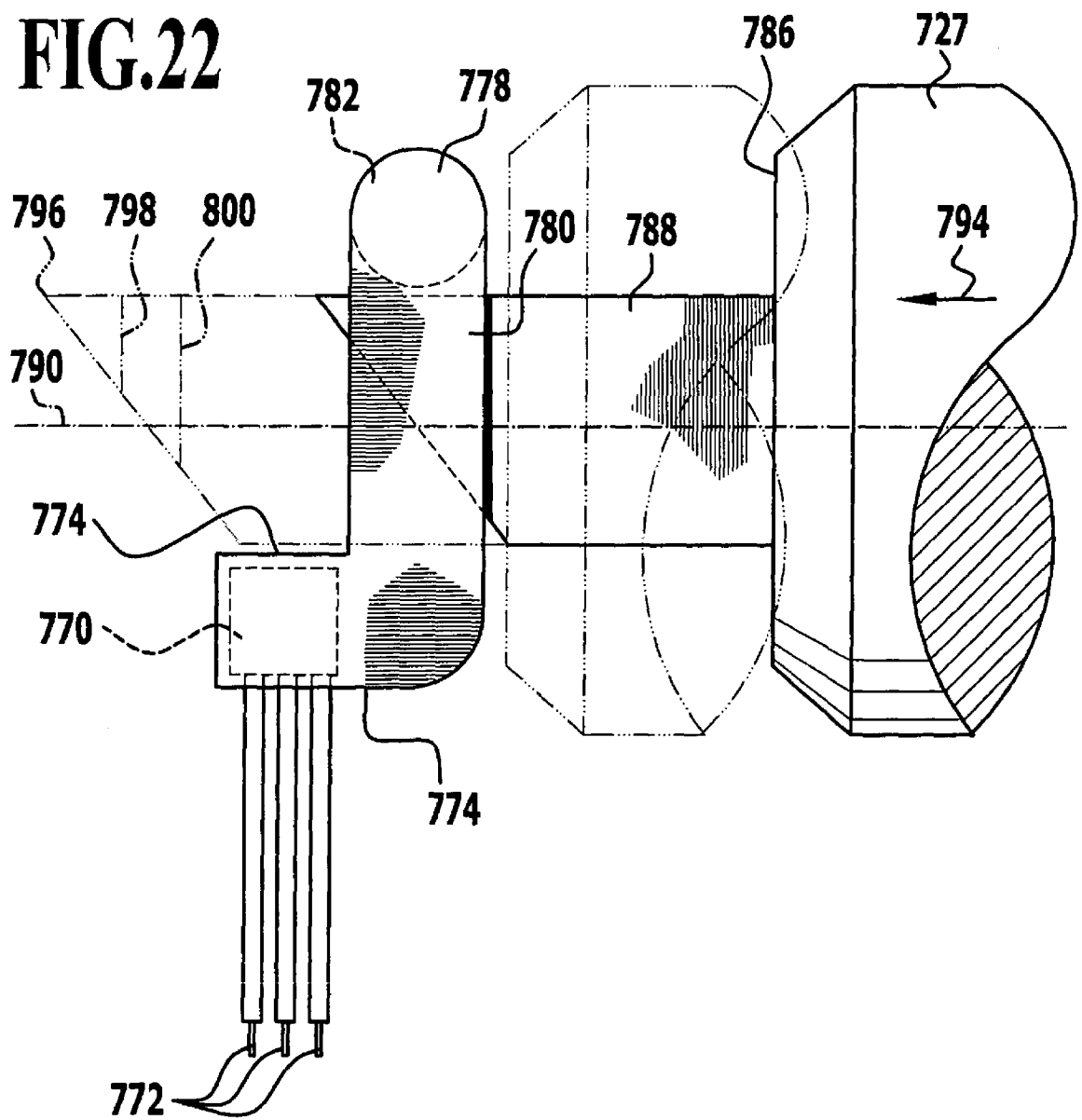
FIG. 22 a schematic representation of a field changing member moved relative to the actuating sensor.

It is shown schematically in FIGS. 21 and 22, for example, for the power/speed push-button 726 or for one of the power/speed push-buttons 136, 336 or 536, how with an actuating sensor, for example, the Hall sensor 264, disposed on the power pack, an actuation signal can be contactlessly generated by moving the power/speed push-button 726.

A Hall sensor 770 with three connection contacts 772 serves as actuating sensor. It is positioned between two short legs 774 of two L-shaped soft iron plates 776, which results in a parallelepipedal structure comprised of the legs 774 and the Hall sensor 770 disposed between these and, possibly, further soft iron elements filling out a space between the legs 774. Disposed between free ends 778 of two long legs 780 of the two soft iron plates 776 is a cylindrical bar magnet 782, as provided, for example, on the power and control unit 110 in the form of the bar magnet 266. In its entirety, this results in a frame-shaped structure, which defines an opening 784 delimited by the long legs 780, the bar magnet 782 and the short legs 774 with the Hall sensor 770 lying between these, as provided, for example, on the power and control unit 110 in the form of the opening 272, with a rectangular cross section. Disposed on the push-button 726 shown schematically in FIG. 21, on an end face 786 of the main body 725 that faces away from an actuating button 727, is a parallelepipedal soft iron element 788, as provided, for example, on the power and control unit 110 in the form of the parallelepipedal soft iron element 270. The parallelepipedal soft iron element 788 protrudes in the direction of a longitudinal axis 790 of the main body 725, and an end face 792 of the parallelepipedal soft iron element 788 is inclined through 450 relative to the end face 786 of the main body 725.

The frame structure with the Hall sensor 770 is so disposed relative to the push-button 726 that as a result of actuation of the push-button 726 in the direction of arrow 794 in FIG. 21, i. e., parallel to the longitudinal axis 790, the main body 725 can be moved with the parallelepipedal soft iron element 788 into the opening 784. Owing to its shape, the ferromagnetic, parallelepipedal soft iron element 788 has, starting from a front end edge 796, cross sections which increase parallel to the end face 786, which is indicated by the two cutting planes 798 and 800 drawn in FIG. 22, which both extend parallel to the end face 786.

When the parallelepipedal soft iron element 788 is moved into the opening 784, this affects the magnetic flux within the return path system formed by the two soft iron plates 776, which couples the bar magnet 782 with the Hall sensor 770. A change in the magnetic flux passing through the Hall sensor 770 leads to a change in the Hall voltage generated by the Hall sensor 770, which can be tapped via the connection contacts 772. The measured Hall voltage, which is used as actuation signal, is then processed by the motor controller 724 into corresponding control signals for the motor 714.

The two push-buttons 726 and 728 are so disposed that they remain, in particular, in a battery-operated drive machine, and the power and control unit 720 can be removed with the motor controller 724 and the battery 722 before sterilization of the accumulator machine 700. The push-button unit 729, which comprises the field changing members in the form of the parallelepipedal soft iron elements 788, thus remains on the accumulator machine 700. Therefore, no electrical contacts that are required for generating an actuation signal remain within the accumulator machine 700, for with control electronics, for example, in the form of motor controller 724, the Hall sensors 770 are also completely removed. The special arrangement of the Hall sensor 770 relative to the bar magnet 782 allows their spatial allocation to be fixed in a definite and permanent manner. A readjustment, as in conventional systems, is not necessary. Any manufacturing tolerances in the size and shape of the parallelepipedal soft iron element 788 and the opening 784 have a far less critical effect on operation of the push-button unit 729 than is the case in conventional systems with a magnet mounted on the push-button and moved relative to the Hall sensor 770.

Figure 23:
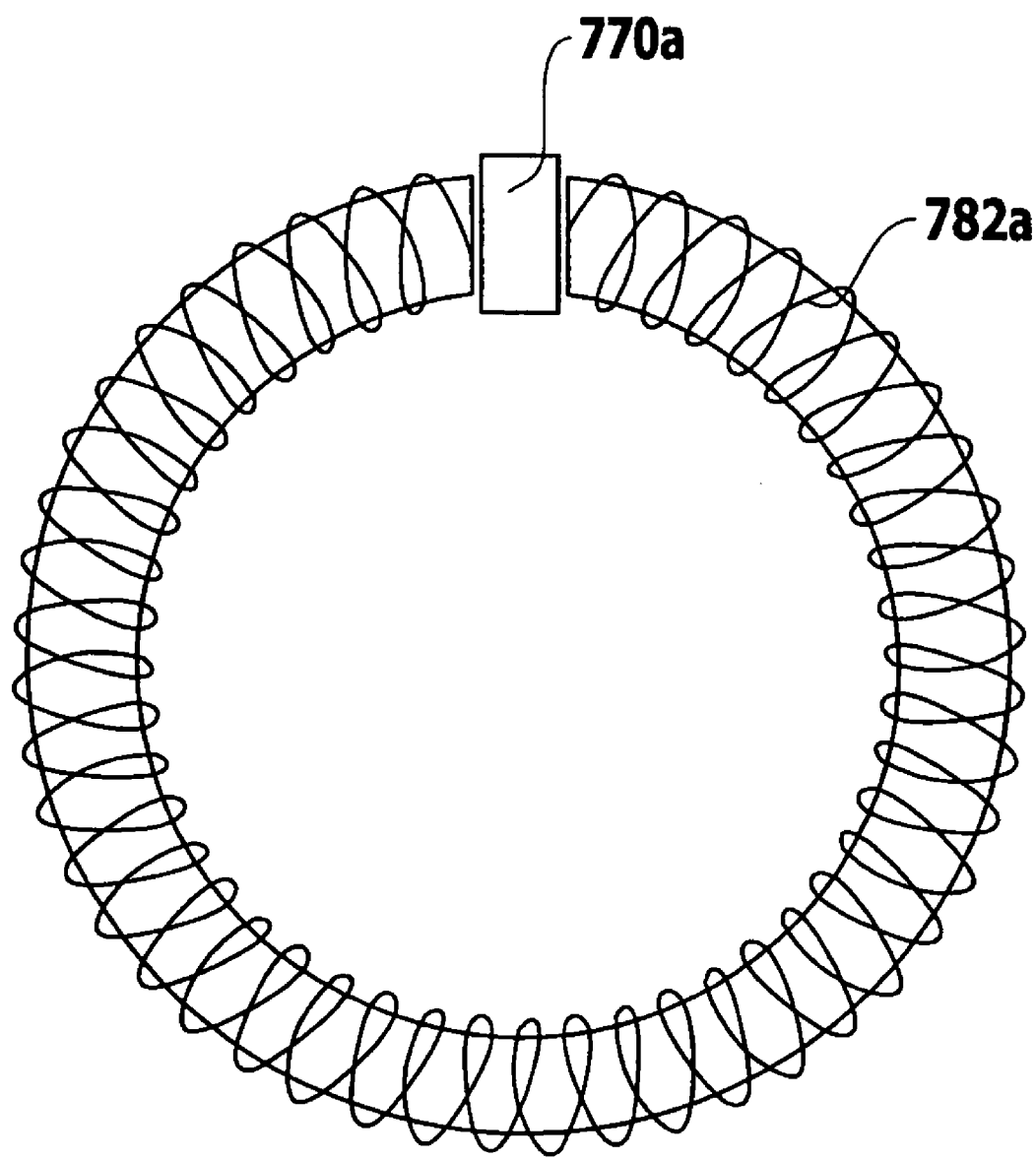
FIG. 23 an example embodiment of an actuating sensor disposed in a gap of a ring coil.

In an alternative to the arrangement of the hall sensor 770 and bar magnet 782 discussed above, as shown in FIG. 23, an actuating sensor (e.g., a hall sensor) 770*a* may be disposed in a gap of a ring coil 782*a*. The actuating sensor 770*a* and ring coil 782*a* operate similarly to the hall sensor 770 and bar magnet 782.

The invention claimed is:

1. Surgical machine comprising:
   a housing,
   a surgical drive disposed in the housing,
   a push-button unit with at least one actuating member mounted on the housing for movement in a direction of actuation for prescribing a rotational speed and/or a direction of rotation of the surgical machine,
   a field generating unit for generating a magnetic field,
   at least one actuating sensor coupled with the field generating unit for generating an actuation signal in response to a movement and/or a position of the actuating member, the generated actuation signal being correlated with a field strength and/or a change in the field generated by the field generating unit, which occurs as a result of a movement of the actuating member,
   a field changing member for generating a change in the field acting at a location of the actuating sensor and generated by the field generating unit, which occurs as a result of a movement and/or a changed position of the actuating member,
   wherein:
   the drive and the housing are directly or indirectly connectable in a detachable manner, and
   the actuating sensor and the field generating unit are fixedly disposed relative to each other.

2. Machine in accordance with claim 1, wherein the push-button unit comprises a frame.

3. Machine in accordance with claim 1, wherein the actuating sensor is a magnetic field sensor.

4. Machine in accordance with claim 3, wherein the magnetic field sensor is a Hall sensor.

5. Machine in accordance with claim 1, wherein the field changing member is at least partially magnetically polarizable and has a magnetic susceptibility $\chi_m$ differing from zero.

6. Machine in accordance with claim 5, wherein the field changing member is at least partially diamagnetic, paramagnetic, ferromagnetic, antiferromagnetic or ferrimagnetic.

7. Machine in accordance with claim 5, wherein the field changing member is a soft iron element.

8. Machine in accordance with claim 1, wherein the field generating unit is a magnet.

9. Machine in accordance with claim 8, wherein the magnet is a permanent magnet.

10. Machine in accordance with claim 8, wherein the magnet is formed by a coil.

11. Machine in accordance with claim 1, wherein the actuating sensor is disposed between poles of the field generating unit.

12. Machine in accordance with claim 11, wherein the actuating sensor is disposed in a gap of a ring coil.

13. Machine in accordance with claim 1, wherein a cross section of the field changing member varies in a direction of actuation of the actuating member.

14. Machine in accordance with claim 13, wherein the cross section increases.

15. Machine in accordance with claim 1, wherein the field generating unit is coupled by a return path system with the actuating sensor.

16. Machine in accordance with claim 15, wherein the return path system is a magnetic return path system.

17. Machine in accordance with claim 1, wherein the field generating unit, the return path system and the actuating sensor define a recess, and the field changing member is so disposed that it is at least partially introducible into the recess as a result of a movement of the actuating member.

18. Machine in accordance with claim 17, wherein the recess has a substantially rectangular cross section.

19. Machine in accordance with claim 1, wherein the actuating member carries the field changing member.

20. Machine in accordance with claim 1, wherein the field generating unit is disposed on a power and control unit.

21. Machine in accordance with claim 1, wherein:
   the machine has at least two different operating modes,
   a first operating mode position of the at least one actuating member being associated with a first operating mode, and
   the at least one actuating member is rotatable about an axis of rotation from the first operating mode position to a second operating mode position, which is associated with a second operating mode of the machine, in order to switch the drive unit over from the first operating mode to the second operating mode.

* * * * *